(12) United States Patent
Donovan et al.

(10) Patent No.: US 11,576,951 B2
(45) Date of Patent: Feb. 14, 2023

(54) STABLE THERAPEUTIC COMPOSITIONS IN APROTIC POLAR SOLVENTS AND METHODS OF MANUFACTURING THE SAME

(71) Applicant: XERIS PHARMACEUTICALS, INC., Chicago, IL (US)

(72) Inventors: Martin Donovan, Chicago, IL (US); Wendy Hu, San Diego, CA (US)

(73) Assignee: XERIS PHARMACEUTICALS, INC., Chicago, IL (US)

( * ) Notice: Subject to any disclaimer, the term of this patent is extended or adjusted under 35 U.S.C. 154(b) by 0 days.

(21) Appl. No.: 16/888,028

(22) Filed: May 29, 2020

(65) Prior Publication Data

US 2020/0376083 A1 Dec. 3, 2020

Related U.S. Application Data

(60) Provisional application No. 62/855,134, filed on May 31, 2019.

(51) Int. Cl.

| | |
|---|---|
| *A61K 38/26* | (2006.01) |
| *A61K 47/02* | (2006.01) |
| *A61K 47/10* | (2017.01) |
| *A61K 47/26* | (2006.01) |
| *A61P 3/10* | (2006.01) |
| *A61K 45/06* | (2006.01) |
| *A61K 9/08* | (2006.01) |
| *A61K 47/20* | (2006.01) |
| *A61K 9/00* | (2006.01) |

(52) U.S. Cl.
CPC ............... *A61K 38/26* (2013.01); *A61K 9/08* (2013.01); *A61K 45/06* (2013.01); *A61K 47/02* (2013.01); *A61K 47/10* (2013.01); *A61K 47/20* (2013.01); *A61K 47/26* (2013.01); *A61P 3/10* (2018.01); *A61K 9/0019* (2013.01)

(58) Field of Classification Search
None
See application file for complete search history.

(56) References Cited

U.S. PATENT DOCUMENTS

| | | | |
|---|---|---|---|
| 4,727,041 A | 2/1988 | Aroonsakul | |
| 5,065,747 A | 11/1991 | Bercu | |
| 9,339,545 B2 | 5/2016 | Prestrelski et al. | |
| 9,649,364 B2 | 5/2017 | Prestrelski et al. | |
| 10,485,850 B2 | 11/2019 | Prestrelski et al. | |

FOREIGN PATENT DOCUMENTS

| | | | | |
|---|---|---|---|---|
| WO | WO-2009024797 A1 | * | 2/2009 | ............. A61K 38/26 |
| WO | WO-2016196976 A1 | | 12/2016 | |
| WO | WO-2016201248 A1 | | 12/2016 | |
| WO | WO-2017053922 A1 | | 3/2017 | |
| WO | WO-2019126753 A1 | | 6/2019 | |

OTHER PUBLICATIONS

Boguszewski, C.L., "Glucagon stimulation test: has its time come?" *Endocrine* 57:361-363, Humana Press, United States (2017).
Cryer, P.E., "Mechanisms of Hypoglycemia-Associated Autonomic Failure and Its Component Syndromes in Diabetes," *Diabetes* 54(12):3592-3601, American Diabetes Association, United States (2005).
"Glucagon in Gastroenterology," Picazo, J., ed., pp. 1-120, MTP Press Ltd., United Kingdom (1979).
International Search Report and Written Opinion of International Application No. PCT/US2020/035172, European Patent Office, Netherlands, dated Aug. 21, 2020, 17 pages.
Seaquist, E.R., et al., "Hypoglycemia and diabetes: a report of a workgroup of the American Diabetes Association and the Endocrine Society," *Diabetes Care* 36(5):1384-1395, American Diabetes Association Inc., United States (2013).
Yuen, K.C.J., "Glucagon stimulation testing in assessing for adult growth hormone deficiency: current status and future perspectives," *International Scholarly Research Notices Endocrinology* 2011(608056):1-6, Hindawi, Egypt (2011).
English language translation of Opposition filed by Laboratorios Legrand S.A. in Columbian Patent Appl. No. NC2021/0016449, dated Oct. 12, 2021, 9 pages.

* cited by examiner

*Primary Examiner* — Christina Bradley
(74) *Attorney, Agent, or Firm* — Sterne, Kessler, Goldstein & Fox P.L.L.C.

(57) ABSTRACT

The present invention concerns the use of aprotic polar solvents, water, and an ionization stabilizing agent to prepare device compatible stable therapeutic formulations by dissolving a therapeutic agent (active ingredient) in an aprotic polar solvent system that can then be used with various devices (e.g., pumps, infusion sets) for administration of the formulation. In certain embodiments, the invention is directed to formulations comprising one or more therapeutic agents, as well as methods of making such formulations, comprising at least one therapeutic agent dissolved in an aprotic polar solvent system, such as a DMSO/water admixture, comprising at least one ionization stabilizing excipient in a concentration sufficient to impart physical and chemical stability to the therapeutic agent.

33 Claims, 1 Drawing Sheet

STABLE THERAPEUTIC COMPOSITIONS IN APROTIC POLAR SOLVENTS AND METHODS OF MANUFACTURING THE SAME

CROSS-REFERENCE TO RELATED APPLICATIONS AND INCORPORATION BY REFERENCE

The present invention claims the priority benefit of U.S. Provisional Application No. 62/855,134, filed May 31, 2019, the disclosure of which is incorporated herein by reference in its entirety.

BACKGROUND OF THE INVENTION

A. Field of the Invention

The present invention is in the field of medical and pharmaceutical arts. Certain embodiments relate generally to plastic and/or rubber compatible therapeutic aprotic solvent formulations comprising one or more active pharmaceutical ingredients that may be used as therapeutic formulations in treating, preventing, and/or diagnosing diseases, disorders and medical conditions in mammals, particularly humans. In particular, the invention concerns the use of aprotic polar solvents, water, and at least one ionization stabilizing agent to prepare device-compatible stable therapeutic formulations by dissolving a therapeutic agent (active pharmaceutical ingredient) in an aprotic polar solvent system that can then be used with various devices for administration of the formulation.

B. Description of Related Art

Parenteral formulations prepared in aprotic polar solvent systems (e.g., a DMSO-based solvent system) benefit from improved drug molecule stability due to the absence of water-mediated degradation pathways. These pathways, including hydrolysis, deamidation and aspartic acid isomerization, are known to be largely responsible for peptide and protein instability in aqueous-based formulations. Furthermore, hydrolysis is also known to promote chemical instability with small molecule drugs. Prior research has demonstrated the improved stability of low moisture peptide and small molecule formulations in DMSO relative to aqueous solutions (see, e.g., U.S. Pat. Ser. Nos. 9,339,545 and 10,485,850, the disclosures of which are incorporated herein by reference in their entireties).

However, one drawback of working with biocompatible organic solvents (e.g., DMSO) is that many commercial materials, e.g., plastics, can be dissolved in these non-aqueous systems. Additionally, organic solvents can be potent extractors of compounds (e.g., antioxidants, plasticizers) used in commercial elastomeric components (e.g., rubber tubing). Consequently, many commercially available container-closure systems (CCS) such as infusion sets and pumps are not compatible with DMSO-based formulations due to dissolution, extraction, and degradation issues.

Alternative approaches to obtaining DMSO-compatible pumps and infusion sets have been to develop specific DMSO compatible components, which are very expensive and require long development and validation timelines.

There remains a need for a formulation platform that couples the stability and solubility provided by aprotic polar solvent systems, while also providing compatibility with a variety of devices, containers, and the like.

BRIEF SUMMARY OF THE INVENTION

Embodiments described herein provide an approach that improves the compatibility of the formulation with materials, devices, containers, and/or one or more flow paths, removing the requirement for expensive specialized components or flow paths. The commercial importance of the compatible formulations is that it enables DMSO-based formulations that are compatible with various plastic and rubber (elastomeric) components used in off-the-shelf and commercially available pumps, infusion sets, containers, etc. In general, formulations prepared from biocompatible organic solvents (e.g., aprotic polar solvents) are often incompatible with the plastic, rubber, and other materials used in devices, containers, and infusion sets.

One advantage that the current formulations have over low moisture DMSO-based formulations, which typically have an upper limit of 10% moisture content, is that it shortens development timelines and reduces the cost associated with producing a solvent compatible infusion set and/or solvent compatible fluid path(s) because there is no need for specialized materials (e.g., plastics, polymers, elastomers) in the flow fluid path. Introducing such compatible materials often requires a considerable expense in terms of time and cost, particularly for devices that have already undergone regulatory review and have been approved for commercial use.

Due to the addition of moisture, the overall stability of the formulation may decline due to increased water-mediated degradation pathways (e.g., hydrolysis). Additionally, some molecules that are prone to gelling and aggregation in aprotic polar solvents such as DMSO (e.g., glucagon) may be more susceptible to some degree of physical instability in a high-moisture solvent-based formulation. It has been discovered that to reduce physical instability in a formulation with a higher moisture content additional protonation (e.g., addition of an acid and/or base) is required, which in turn can increase the rate of chemical degradation. Consequently, a high-moisture formulation may not exhibit comparable long-term stability as a low-to-no added moisture (e.g., less than about 10% water) non-aqueous formulations. However, depending on the application, different stability profiles can be sufficient. For example, a rescue formulation generally requires at least 1-2 years of room-temperature stability, as a patient will need to constantly carry the product with them. On the other hand, a formulation for use in a pump-based delivery system can be stored long-term in a refrigerator or freezer and removed from low-temperature storage prior to use in a pump. Accordingly, this type of formulation may only require short-term room-temperature stability (1-3 months) and even shorter-term high temperature stability (e.g., 3-7 days at on-body or body temperature (35-37° C.), as the formulation will be stored in the pump during the time that the pump is adhered to the patient). For the latter type of application, data from the high-moisture formulations presented herein indicate it is a viable approach to improving compatibility with commercially used materials, such as plastics and elastomeric (rubber) components. The development of formulations that maintain sufficient physical and chemical stability of a therapeutic molecule in the presence of a high-moisture content (e.g., >10%) is described herein.

An additional advantage of increased moisture aprotic polar solvent-based formulations is a low freezing point obtained with such solvent systems. For example, pure DMSO freezes at 18° C., while water freezes at 0° C. However, when mixed together, DMSO and water form a mixture that exhibits a minimum freezing point of approximately −70° C. at approximately 30-35% (w/w) added moisture. A benefit of this low freezing point is that these formulations could be stored in a refrigerator (2-8° C.) or freezer (−20° C.) for long-term storage (which will inhibit chemical degradation) without undergoing any freeze-thaw cycles that may promote physical and chemical instability.

Certain embodiments are directed to aprotic polar solvent formulations comprising: (a) a therapeutic agent; (b) an ionization stabilizing excipient; (c) an aprotic polar solvent; and (d) greater than 10% v/v to about 50% v/v water. In particular aspects, the moisture content is 20, 25, 30, 35 to 40% v/v, including all values and ranges there between. In certain aspects, the aprotic solvent formulation is compatible with a container and/or device flow path. In certain instances, the aprotic polar solvent at a concentration greater than 85% v/v to 100% v/v is incompatible with the device flow path. In certain aspects, aprotic polar solvent is present at most or at about 85, 80, 75, 70, 65, 60, 55, to 50% v/v, including all values and ranges there between. In certain aspects, the components of the device flow path can comprise rubber, elastomers, thermoplastic, thermoset plastic, polystyrenes, polyvinyl alcohols, polyvinyl pyrrolidones, polyalkylene oxides, acrylamides, acrylic acids, cellulose, cellulose ethers, cellulose esters, cellulose amides, polyvinyl acetates, polycarboxylic acids, polyamides, polyacrylamide, copolymers of maleic/acrylic acids, polysaccharides, natural gums, and/or other solvent incompatible materials. The components of the device flow path can include one or more of polycarbonate (PC), acrylonitrile butadiene styrene (ABS), meta-acrylonitrile butadiene styrene (MABS), polyethylene terephthalate glycol (PETG), poly-cyclohexylenedimethylene terephthalate glycol (PCTG), polyethylene terephthalate (PETE), dimethylcellulose, carboxymethylcellulose sodium, dextrin, ethylcellulose, hydroxyethyl cellulose, hydroxypropyl methylcellulose, maltodextrin, polymethacrylates, polystyrene (PS), polyisobutylene (PIB), polymethyl methacrylate (PMMA), ethylene vinyl acetate (EVA), polyvinyl chloride (PVC), thermoplastic polyurethane (TPU), hydroxypropyl methyl cellulose (HPMC), high density polyethylene (HDPE), low density polyethylene (LDPE), polyurethane, or blends thereof.

In certain aspects, the therapeutic agent is a peptide or salt thereof. In certain instances, the peptide is administered by infusion (continuous or intermittently) over time, e.g., over at least 1, 2, 3, 4, 5, 6, 7, 8, 9, 10, 11, 12, 13, 15, 16, 17, 18, 19, 20, 21, 22, 23, 24, 25, 26, 27, 28, 29, 30 hours, or over a period of multiple days, for example, 1 day to 1 week (i.e., one day, two days, three days, four days, five days, six days and up to seven days). The peptide or salt thereof can be dissolved in an amount from about 0.01, 0.1, 0.5, 1.0, 1.5, 2.0, 3.0, 5.0 mg/mL up to the solubility limit of the peptide or salt thereof. In certain aspects, the peptide is a glucagon peptide, glucagon analog, glucagon mimetic, or salt thereof.

At least one ionization stabilizing excipient can be dissolved in the aprotic solvent in an amount to stabilize the ionization of the therapeutic agent. In certain aspects, the ionization stabilizing excipient is at a concentration of 0.01 mM to less than 200 mM. The ionization stabilizing excipient can be, but is not limited to, a mineral acid. The mineral acid can be selected from hydrochloric acid, sulfuric acid, nitric acid and phosphoric acid. The ionization stabilizing excipient may also be an organic acid (acids having a carboxylic acid —COOH functional group). Non-limiting examples of organic acids include acetic acid, citric acid, and amino acids. In certain aspects, the aprotic solvent is DMSO. In particular aspects, the ionization stabilizing excipient is a mineral acid and the aprotic solvent is DMSO.

The formulations can further include a preservative at less than 10, 5, or 3% w/v. In certain aspects, the preservative is benzyl alcohol.

The formulations can further include a disaccharide at less than 10, 5, or 3% w/v. In particular aspects, the disaccharide is trehalose.

In certain embodiments, the formulation can have freezing point less than 0° C., preferably less than −20° C., or more preferably between −50° C. to −70° C.

The formulations can be compatible with various devices that store and/or administer the formulations. Non-limiting examples include a device comprising an infusion set connected to a pump capable of parenterally administering the formulation to a subject.

Alternatively, the device may be a patch pump that is directly attached to the patient and does not require an external infusion set.

Certain embodiments are directed to methods of treating hypoglycemia by administering an effective amount of a formulation described herein to a subject in need thereof. In certain aspects, the formulations administered are provided or stored in a device or container that comprises components that are not compatible with a formulation having an aprotic polar solvent in an amount of greater than 90% (v/v) of the formulation. In certain aspects, the formulation is administered by infusion. In particular aspects, the administration is by infusion via a pump which may be connected in series to an infusion set. The infusion can be a continuous and/or bolus pump infusion.

Certain embodiments are directed to methods of stably formulating a glucagon peptide comprising the steps of: (a) mixing at least one ionization stabilizing excipient with an aprotic solvent to form an ionization stabilizing excipient/aprotic solvent mixture; (b) dissolving a therapeutic agent in the ionization stabilizing excipient/aprotic solvent mixture; and (c) adding water to the ionization stabilizing excipient/aprotic solvent mixture resulting in a moisture content of between greater than 10% v/v and about 80% v/v, preferably between about 20% v/v to about 50% v/v, forming a device flow path compatible aprotic solvent formulation. In certain aspects, the ionization stabilizing excipient is hydrochloric acid, nitric acid, sulfuric acid, or a combination thereof. The ionization stabilizing excipient can be, but need not be, at a concentration between 0.1 mM to 200 mM.

Without wishing to be bound by theory, these increased-moisture aprotic polar solvent solutions (e.g., DMSO based solutions) provide for a therapeutic to be preferentially surrounded by non-water solvent molecules, which strongly solvate the therapeutic via formation of hydrogen bonds (where the aprotic polar solvent is a strong hydrogen bond acceptor, and the therapeutic (e.g., the backbone amines) act as hydrogen bond donors). The moisture may displace some of the solvent molecules solvating the peptide, but the therapeutic will remain preferentially associated with the non-water solvent, thereby excluding the water, which may then mostly interact with the container (i.e., the plastic and rubber components of the infusion set or pump fluid path). The decreased interaction of the non-water solvent with the container promotes compatibility, while the interaction of the non-water solvent with the therapeutic allows the formulation to maintain acceptable physical and chemical stability that exceeds the stability of comparable aqueous formulations.

The moisture content required to promote compatibility with a device can vary (e.g., depending on the materials comprising the fluid flow path of the device). In certain embodiments, the moisture content can be greater than 10%, for example about 15%, about 20%, about 25%, about 30%, about 35%, about 40%, about 45%, about 50%, about 55%, about 60%, about 65%, about 70%, about 75% and about 80% (all v/v), including all values and ranges therebetween. In certain aspects, the moisture content can be between about 20%, about 25%, about 30%, about 35%, about 40%, and about 45%, to about 50% (all v/v), including all values and ranges there between. Thus, as used herein, an "aprotic polar solvent system" includes at least one aprotic polar solvent (e.g., DMSO) and water to yield a final moisture content of between greater than 10% to about 80% (v/v).

Therapeutic molecules typically require an optimal or beneficial ionization profile in order to exhibit prolonged stability when solubilized in an aprotic polar solvent system. Maintaining the beneficial ionization profile of a therapeutic molecule dissolved in an aprotic polar solvent system can be achieved by using at least one ionization stabilizing excipient. Certain embodiments of the present invention are directed to methods for preparing flow path compatible stable formulations containing at least one therapeutic molecule solubilized in an aprotic polar solvent system. In certain aspects, the therapeutic molecule is not required to be previously dried from a buffered aqueous solution prior to reconstitution in the aprotic polar solvent system.

The ability to use existing (e.g., commercially available) devices and the ability to circumvent the need for drying a therapeutic molecule (e.g., a peptide) from a buffered aqueous solution can save considerable time and cost throughout the various product development stages.

Stable solutions of a therapeutic agent(s) solubilized in non-aqueous aprotic polar solvents (e.g., DMSO) can be prepared by adding a specific amount of a compound, or combination of compounds, that function as an ionization stabilizing excipient. Without wishing to be bound by theory, it is believed that the ionization stabilizing excipient can act as a proton source (e.g., a molecule that can donate a proton to the therapeutic molecule) in the aprotic polar solvent system that may protonate the ionogenic groups on the therapeutic molecule such that the therapeutic molecule possesses an ionization profile having an improved physical and chemical stability in the aprotic polar solvent system. Alternatively, the ionization stabilizing excipient can act as a proton sink (e.g., a molecule or moiety that can accept/remove a proton from the therapeutic molecule) such that the therapeutic molecule possesses an ionization profile having an improved physical and chemical stability in the aprotic polar solvent system. In one aspect of the present invention, there is disclosed a stable formulation for parenteral injection. Alternatively, transdermal delivery such as through topical application to skin can be used.

Certain embodiments are directed to a formulation of a therapeutic agent comprising a therapeutic agent at a concentration of at least, at most, or about 0.1 mg/mL, about 1 mg/mL, about 5 mg/mL, about 10 mg/mL, about 15 mg/mL, about 20 mg/mL, about 25 mg/mL, about 50 mg/mL, or about 100 mg/mL, to about 150 mg/mL, about 200 mg/mL, about 300 mg/mL, about 400 mg/mL, or about 500 mg/ml, or even higher concentrations up to the solubility limit of the therapeutic agent in the aprotic polar solvent system comprising a concentration of at least one ionization stabilizing excipient that provides physical and chemical stability to the therapeutic agent. In certain aspects, the therapeutic agent is a peptide. In further aspects, the therapeutic agent is a small molecule. The formulation can comprise an ionization stabilizing excipient at a concentration of at least, at most, or about 0.01, 0.1, 0.5, 1, 10, or 50 mM to 10, 50, 75, 100, 500, 1000 mM, or up to the solubility limit of the ionization stabilizing excipient in the aprotic polar solvent system. In certain aspects, the ionization stabilizing excipient concentration is between about 0.1 mM to about 100 mM, particularly about 1 mM to about 10 mM, e.g., about 1 mM, about 2 mM, about 3 mM, about 4 mM, about 5 mM, about 6 mM, about 7 mM, about 8 mM, about 9 mM and about 10 mM. In certain embodiments, the ionization stabilizing excipient may be a suitable mineral acid, such as hydrochloric acid, sulfuric acid, nitric acid and the like. In certain aspects, the ionization stabilizing excipient may be an organic acid, such as an amino acid, amino acid derivative, or the salt of an amino acid or amino acid derivative (examples include glycine, trimethylglycine (betaine), glycine hydrochloride, and trimethylglycine (betaine) hydrochloride). In a further aspect, the amino acid can be glycine or the amino acid derivative trimethylglycine. In certain aspects, a peptide is less than 150, 100, 75, 50, or 25 amino acids. In further aspects, the aprotic solvent system comprises DMSO. The aprotic solvent can be deoxygenated, e.g., deoxygenated DMSO. In certain embodiments, the formulation may be prepared by first adding the ionization stabilizing excipient to the aprotic polar solvent system, followed by addition of the therapeutic molecule. Alternatively, the therapeutic molecule may initially be solubilized in the aprotic polar solvent system followed by addition of the ionization stabilizing excipient. In a further aspect, the ionization stabilizing excipient and the therapeutic molecule may be solubilized simultaneously in the aprotic polar solvent system. In certain aspects, the therapeutic agent is glucagon, a glucagon analogue, or salt thereof.

Other embodiments of the present invention are directed to methods of stably formulating a therapeutic agent (e.g., a peptide or a small molecule) comprising the steps of: (a) calculating or determining the appropriate ionization stabilizing excipient (e.g. proton concentration) needed to achieve a stabilizing ionization profile of a target therapeutic agent (e.g., a peptide(s) or small molecule(s)) in an aprotic polar solvent system; (b) mixing at least one ionization stabilizing excipient with the aprotic polar solvent system to attain an appropriate ionization environment that provides the ionization profile determined in step (a); and (c) solubilizing the target therapeutic agent(s) in the aprotic solvent having an appropriate environment to physically and chemically stabilize the therapeutic agent. In certain non-limiting aspects, the therapeutic agent is chemically or physically stable for at least or about 0.25, 0.5, 1, 2, 3, 4, or 5 years, and more preferably about 0.25 to about 2 years, at room temperature, at refrigerated temperatures (e.g., about 2° C. to about 10° C. or about 2° C., about 3° C., about 4° C., about 5° C., about 6° C., about 7° C., about 8° C., about 9° C. or about 10° C.), or at sub-zero temperatures (e.g., about −4° C. to about −80° C., or about −4° C., about −10° C., about −15° C., about −20° C., about −25° C., about −40° C., about −45° C., about −50° C., about −60° C., about −70° C., or about −80° C.). In certain aspects, the dissolution of the therapeutic agent and the addition of the ionization stabilizing excipient to the aprotic polar solvent system can be done in any order or concurrently, thus the ionization stabilizing excipient can be mixed first followed by dissolution of the therapeutic agent, or the therapeutic agent can be dissolved followed by addition of the ionization stabilizing excipient to the solution, or the ionization stabilizing excipient and the therapeutic agent can be added or dissolved in an aprotic polar solvent system concurrently. In further aspects, the order of addition of the water to the aprotic polar solvent(s) may be performed prior to or following addition of the therapeutic agent(s) and/or ionization stability excipient(s). As a non-limiting example, for therapeutic agent(s) having limited aqueous solubility, it may be necessary to initially dissolve the therapeutic agent(s) in the aprotic polar solvent(s) at an excess concentration (i.e., above target/final formulation concentration), and then incorporate the water such that the targeted concentrations of the therapeutic compound and moisture are achieved in the finished composition or formulation. The ionization stabilizing excipient(s) may be added to the mixture prior to or following addition of the water. In some embodiments, the addition of the ionization stabilizing excipient(s) may be added prior to addition of the therapeutic agent to promote dissolution in the aprotic polar solvent system. Additional formulation components (e.g., preservatives, surfactants, etc.) may be incorporated into the formulation either prior to or following addition of the therapeutic agent. In a further aspect, the entire amount of a component (e.g., a therapeutic agent or an ionization stabilizing excipient) need not to be mixed at a particular point; that is, a portion of the one or more components can be mixed first, second, or concurrently, and another portion mixed at another time, first, second, or concurrently. In certain aspects, the therapeutic agent can be a peptide, and the ionization stabilizing excipient may be a suitable mineral acid, such as hydrochloric acid, sulfuric acid, and/or nitric acid. In certain aspects, the peptide(s) is less than 200, 150, 100, 75, 50, or 25 amino acids. The concentration of the therapeutic agent and/or ionization stabilizing excipient added to the solution can be between 0.01, 0.1, 1, 10, 100, 1000 mM, or up to its solubility limit, including all values and ranges there between. In certain aspects, the aprotic polar solvent system is deoxygenated. In a further aspect, the aprotic polar solvent in the solvent system comprises, consists essentially of, or consists of DMSO or deoxygenated DMSO.

In a further aspect of the present invention, there is disclosed a method for treating or preventing a condition, disease, disorder, etc. comprising administering to a subject in need thereof a formulation(s) of the present invention in an amount effective to treat or prevent the condition, disease, disorder, etc. Any suitable dosage of a therapeutic agent (e.g., protein, peptide, or small molecule) may be administered in the methods of the present invention. The dosage administered will, of course, vary depending upon known factors, such as the pharmaco-dynamic characteristics of the particular compound, salt, or combination; the age, health, or weight of the subject; the nature and extent of symptoms; the metabolic characteristics of the drug and patient, the kind of concurrent treatment; the frequency of treatment; or the effect desired. In certain aspects, hypoglycemia can be treated by administering a formulation described herein comprising an effective amount of glucagon.

The stable formulations described herein are useful for the parenteral injection of any therapeutic agent (protein, peptide, and/or small molecule) that has limited or poor stability or solubility in an aqueous environment. In certain aspects, a formulation as described herein is provided in as an injectable formulation. The injectable formulation can be administered into the epidermal, dermal, subcutaneous or intramuscular layer of a patient. In certain aspects, the formulations are administered intracutaneously.

Thus, in some embodiments, the therapeutic agent or peptide or salt thereof is selected from the group consisting of glucagon, pramlintide, insulin, icatibant, leuprolide, an LHRH agonist, parathyroid hormone (PTH), amylin, botulinum toxin, hematide, an amyloid peptide, cholecystokinin, a conotoxin, a gastric inhibitory peptide, an antibody (which may be monoclonal or polyclonal) or a fragment thereof, an immunogenic peptide (e.g., a peptide or peptide complex derived from a virus, a bacterium, or any prokaryotic or eukaryotic organism or cell thereof), an insulin-like growth factor, a growth hormone releasing factor, an anti-microbial factor, glatiramer, glucagon-like peptide-1 (GLP-1), a GLP-1 agonist, exenatide, analogs thereof, and mixtures thereof. In one embodiment, the peptide is glucagon or a glucagon analog or a glucagon peptidomimetic. In another embodiment, the peptide is parathyroid hormone. In yet another embodiment, the peptide is leuprolide. In still another embodiment, the peptide is glatiramer. In yet another embodiment, the peptide is icatibant. In yet another embodiment, a first peptide is pramlintide and a second peptide is insulin. In still another embodiment, the first peptide is glucagon and the second peptide is exenatide. In other embodiments, the stable formulations used in accordance with the present invention comprise co-formulations or mixtures of the types of compounds described herein, such as at least one peptide, at least one small molecule, and combinations thereof.

Definitions

The terms "container," "reservoir," "infusion set," "pump," "formulation-flow path," "fluid flow path," etc. should be interpreted as interchangeable and equivalent being these components will be in direct contact with the formulations being administered or stored with potential to interact with the components and their surfaces. The terms imply any and all components that the formulation will contact during storage (e.g., pump reservoir) and delivery (e.g., fluid flow path in pump and the infusion set when connected in series to a pump). The term "infusion set" as used herein may be interpreted to include both internal infusion sets (i.e., those contained within patch pumps) as well as complete tubing systems that connect a pump to the pump user and are generally external to the pump. In certain configurations, external infusion sets include a cannula (e.g., for subcutaneous administration), an adhesive mount, quick-disconnect, and a pump cartridge connector (for example, a Luer-type connector).

The term "dissolution," as used herein, refers to a process by which a material(s) in a gas, solid, or liquid state becomes a solute(s), a dissolved component(s), of a solvent, forming a solution of the gas, liquid, or solid in the solvent. In certain aspects, a therapeutic agent or an excipient, e.g., an ionization stabilizing excipient, is present in an amount up to its solubility limited or is fully solubilized. The term "dissolve" refers to a gas, liquid, or solid becoming incorporated into a solvent to form a solution.

The term "elastomer," as used herein, refers to a natural or synthetic polymer having elastic properties. The terms "elastomer" and "rubber" may be used interchangeably herein.

The term "excipient," as used herein, refers to a natural or synthetic substance formulated alongside the active or therapeutic ingredient (an ingredient that is not the active ingredient) of a medication, included for the purpose of stabilization, bulking, or to confer a therapeutic enhancement on the active ingredient in the final dosage form, such as facilitating drug absorption, reducing viscosity, enhancing solubility, adjusting tonicity, mitigating injection site discomfort, depressing the freezing point, or enhancing stability. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life.

"Small molecule drugs" in the context of the present invention are biologically active compounds (and salts thereof) that can bring about a desired, beneficial, and/or pharmacological effect on a subject. These "small molecule drugs" are organic or inorganic compounds. Therefore, the small molecule drugs in the context of the present invention are not polymeric compounds. Typically, the small molecule drugs have a molecular weight of less than approximately 1000 Daltons. Certain small molecule drugs are "moisture sensitive" in that they are increasingly unstable in the presence of water. Also, salts that can be used with the small molecule drugs are known to those skilled in the art and include salts with inorganic acids, organic acids, inorganic bases, or organic bases.

The term "therapeutic agent" or "therapeutic" encompasses proteins, peptides, small molecule drugs, and pharmaceutically acceptable salts thereof. Useful salts are known to those skilled in the art and include salts with inorganic acids, organic acids, inorganic bases, or organic bases. Therapeutic agents useful in the present invention are those protein, peptide, and small molecule compounds that affect a desired, beneficial, and often pharmacological, effect upon administration to a human or an animal, whether alone or in combination with other pharmaceutical excipients or inert ingredients.

The term "peptide" and "peptide compound" refers to amino acid or amino acid-like (peptidomimetics) polymers of up to about 200 amino acid residues bound together by amide (CONH) or other linkages. In certain aspects, a peptide can be up to 150, 100, 80, 60, 40, 20, or 10 amino acids. "Protein" and "protein compound" refer to polymers of greater than 200 amino acid residues bound together by amide linkages. Analogs, derivatives, agonists, antagonists, and pharmaceutically acceptable salts of any of the peptide or protein compounds disclosed here are included in these terms. The terms also include peptides, proteins, peptide compounds, and protein compounds that have D-amino acids, modified, derivatized, or naturally occurring amino acids in the D- or L-configuration and/or peptomimetic units as part of their structure.

"Analogue" and "analog," when referring to a peptide or protein, refers to a modified peptide or protein wherein one or more amino acid residues of the peptide or protein have been substituted by other amino acid residues, or wherein one or more amino acid residues have been deleted from the peptide or protein, or wherein one or more amino acid residues have been added to the peptide or protein, or any combination of such modifications. Such addition, deletion, or substitution of amino acid residues can take place at any point, or multiple points, along the primary structure comprising the peptide, including at the N-terminal of the peptide or protein and/or at the C-terminal of the peptide or protein.

"Derivative," in relation to a parent peptide or protein, refers to a chemically modified parent peptide or protein or an analog thereof, wherein at least one substituent is not present in the parent peptide or protein an analog thereof. One such non-limiting example is a parent peptide or protein which has been covalently modified. Typical modifications are amides, carbohydrates, alkyl groups, acyl groups, esters, pegylations and the like.

"Single-phase solution" refers to a solution prepared from a therapeutic agent that is dissolved in a solvent, or solvent system (e.g., mixture of two or more solvents (e.g. solvent and a co-solvent)), wherein the therapeutic agent is completely dissolved in the solvent or solvent system and there is no longer particulate matter visible, such that the solution can be described as optically clear. A single-phase solution may also be referred to as a "single-phase system," and is distinguished from a "two-phase system" in that the latter is comprised of particulate matter (e.g. powder) suspended in a fluid.

"Inhibiting" or "reducing," or any variation of these terms, includes any measurable decrease or complete inhibition to achieve a desired result.

"Effective" or "treating" or "preventing," or any variation of these terms, means adequate to accomplish a desired, expected, or intended result.

"Chemical stability," when referring to a therapeutic agent, refers to an acceptable percentage of degradation products produced by chemical pathways such as oxidation and/or hydrolysis and/or fragmentation and/or other chemical degradation pathways. In particular, a formulation of the type described herein may be considered chemically stable if no more than about 20% breakdown products are formed after at least one year of storage at the intended storage temperature of the product (e.g., refrigerated storage or subzero storage); or storage of the product at accelerated conditions (25° C./60% relative humidity) for one month, two months or preferable three months. In some embodiments, a chemically stable formulation has less than 30%, less than 25%, less than 20%, less than 15%, less than 10%, less than 5%, less than 4%, less than 3%, less than 2%, or less than 1% breakdown products formed after an extended period of storage at the intended storage temperature of the product.

"Physical stability," when referring to a therapeutic agent, refers to an acceptable percentage of aggregates (e.g., dimers, trimers and larger forms) being formed. In particular, a formulation is considered physically stable if no more than about 15% aggregates are formed after at least one year of storage at the intended storage temperature of the product (e.g., refrigerated storage or subzero storage); or storage of the product at 25° C./60% relative humidity for one month, two months, and preferably three months. In some embodiments, a physically stable formulation has less than less than 15%, less than 10%, less than 5%, less than 4%, less than 3%, less than 2%, or less than 1% aggregates formed after an extended period of storage at the intended storage temperature of the product.

"Stable formulation" refers to a formulation where at least about 65% of the therapeutic agents (e.g., peptides or salts thereof) remain chemically and physically stable after at least one month of storage at room temperature, or up to at least one year of storage at refrigerated or subzero temperatures. Particularly preferred formulations are those in which at least about 80%, 85%, 90%, 91%, 92%, 93%, 94%, 95%, 96%, 97%, 98%, or 99% chemically and physically stable therapeutic agent remains under these storage conditions. Especially preferred stable formulations are those which do not exhibit degradation after sterilizing irradiation (e.g., gamma, beta, or electron beam).

As used herein, "parenteral injection" refers to the administration of therapeutic agents (e.g., peptides or small molecules) via a route other than the alimentary canal—any administration that is not by way of the digestive tract—for example, intravenous infusion, intranasal administration, buccal administration, transdermal administration, or injection under or through one or more layers of skin or mucus membranes of an animal, such as a human. Standard parenteral injections are given into the subcutaneous, intramuscular, or intradermal tissues of an animal, e.g., a human. These deep locations are targeted because the tissue expands more easily relative to shallow dermal sites to accommodate injection volumes required to deliver most therapeutic agents, e.g., 0.1 to 3.0 cc (mL).

The term "intracutaneous" encompasses administration into the epidermal, dermal or subcutaneous skin layer.

As used herein, the term "aprotic polar solvent" refers to a polar solvent which does not contain acidic hydrogen and thus does not act as a hydrogen bond donor. Polar aprotic solvents include, but are not limited to dimethylsulfoxide (DMSO), dimethylformamide (DMF), ethyl acetate, n-methyl pyrrolidone (NMP), dimethylacetamide (DMA), and propylene carbonate.

As used herein, the term "aprotic polar solvent system" refers to a solution wherein the solvent is a single aprotic polar solvent (for example, neat DMSO), or a mixture of two or more aprotic polar solvents (for example, a mixture of DMSO and NMP), or a mixture of at least one aprotic polar solvent with another pharmaceutically acceptable solvent system. In additional aspects, the term "aprotic polar solvent system" refers to a solution wherein the solvent is one or more aprotic polar solvents admixed with an amount of moisture, e.g., water, at a v/v ratio of at least about 99.9% aprotic solvent to about 0.1% water, up to a v/v ratio of at least about 50% aprotic solvent to about 50% water.

As used herein, "residual moisture" may refer to the residual moisture (typically, residual water) in the drug powder following preparation by the manufacturer/supplier. Typical powders often have residual moisture contents ranging from up to 10% (w/w). When these powders are dissolved in an aprotic polar solvent system, the residual moisture in the powder is incorporated into the formulation. Additionally, the aprotic polar solvents may also contain a certain level of residual moisture. For example, a freshly opened bottle of USP-grade DMSO may contain up to 0.1% (w/w) moisture. The residual moisture is different from "added moisture," where water is intentionally added to the formulation, for example to serve as a co-solvent, or to depress the freezing point of the aprotic polar solvent system. Moisture may also be introduced into the formulation during addition of an ionization stabilizing excipient (for example, through addition of a mineral acid from an aqueous stock solution (e.g., 1 N HCl or $H_2SO_4$)), or through the addition of water (e.g. water for injection). The total moisture content (% v/v, unless otherwise stated) in a formulation immediately following preparation is due to the contributions from both the residual moisture and the added moisture.

As used herein, "device flow path" refers to a part of a device that can come in contact with a formulation/solution/solvent, during administering the formulation/solution/solvent to a subject using the device. In some aspects, the device can be an infusion set in series with a pump capable of parenterally administering a formulation/solution/solvent to a subject through various needles and/or tubing. In other aspects, the device can be a patch pump that is directly adhered to the patient and which does not require the use of an external infusion set connected in series with the pump.

As used herein, "formulation/solution/solvent compatible with a device flow path" refers that the formulation/solution/solvent is compatible with the components of the device flow path. For formulation/solution/solvent that is compatible with a component, the formulation/solution will dissolve less than 0.05 to 5% of the component when the component is kept in continuous contact with the formulation/solution/solvent for a specific in-use period and storage condition (e.g. one non-limiting example would be an in-use period of 3 days at 37° C. for an on-body pump and/or infusion set). In addition to not dissolving, a component that is compatible with a formulation should not undergo other significant physical changes (e.g. discoloration, loss of clarity such as going from clear to partially opaque, become excessively brittle/soft or rigid/inflexible) when in contact with the formulation under the specified in-use period and condition, e.g., for a time period of 12 to 72 hours at a temperature of 25 to 40° C.

As used herein, "formulation/solution/solvent incompatible with a device flow path" means that the formulation/solution/solvent is incompatible with one or more components of the device flow path. For formulation/solution/solvent that is incompatible with a component, the formulation/solution/solvent is capable of dissolving at least 1 to 20% of the component during a given in-use period and storage condition, e.g., within 12 to 24 hours at a temperature of 25 to 40° C. or less when the component is kept in continuous contact with the formulation/solution/solvent.

The term "about" or "approximately" or "substantially unchanged" are defined as being close to as understood by one of ordinary skill in the art, and in one non-limiting embodiment the terms are defined to be within 10%, preferably within 5%, more preferably within 1%, and most preferably within 0.5%. Further, "substantially non-aqueous" refers to less than 5%, 4%, 3%, 2%, 1%, or less by weight or volume of water.

"Pharmaceutically acceptable" ingredient, excipient or component is one that is suitable for use with humans and/or animals without undue adverse side effects (such as toxicity, irritation and allergic response) commensurate with a reasonable benefit/risk ratio.

"Pharmaceutically acceptable carrier" means a pharmaceutically acceptable solvent, suspending agent, or vehicle for delivering a drug compound of the present invention to a mammal such as a human.

As used herein, an "ionization stabilizing excipient" is an excipient that establishes and/or maintains a particular ionization state for a therapeutic agent. In certain aspects, the ionization stabilizing excipient can be, or includes, a molecule that donates at least one proton under appropriate conditions or is a proton source. According to the Bronsted-Lowry definition, an "acid" is a molecule that can donate a proton to another molecule, which by accepting the donated proton may thus be classified as a base. In other aspects, the ionization stabilizing excipient can be, or includes, a molecule that accepts at least one proton under appropriate conditions or is a proton sink. According to the Bronsted-Lowry definition, a "base" is a molecule that can accept a proton from another molecule, which by donating the accepted proton may thus be classified as an acid. As used in this application, and as will be understood by the skilled technician, the term "proton" refers to the hydrogen ion, hydrogen cation, or $H^+$. The hydrogen ion has no electrons and is composed of a nucleus that typically consists solely of a proton (for the most common hydrogen isotope, protium). Specifically, a molecule that can donate a proton to the therapeutic agent is considered an acid or proton source, regardless of whether it is completely ionized, mostly ionized, partially ionized, mostly unionized, or completely unionized in the aprotic polar solvent.

As used herein, a "mineral acid" is an acid that is derived from one or more inorganic compounds. Accordingly, mineral acids may also be referred to as "inorganic acids." Mineral acids may be monoprotic or polyprotic (e.g. diprotic, triprotic, etc.). Non-limiting examples of mineral acids include hydrochloric acid (HCl), nitric acid ($HNO_3$), sulfuric acid ($H_2SO_4$), and phosphoric acid ($H_3PO_4$).

As used herein, a "mineral base" (which may be equally and alternatively referred to as an "inorganic base") is a base that is derived from one or more inorganic compounds. Many, but not all, inorganic bases are generally classified as "strong bases," and non-limiting examples of inorganic bases include sodium hydroxide (NaOH), potassium hydroxide (KOH), magnesium hydroxide ($Mg(OH)_2$) and calcium hydroxide ($Ca(OH)_2$).

As used herein, an "organic acid" is an organic compound with acidic properties (i.e. can function as a proton source). Carboxylic acids, such as acetic acid or citric acid, are one example of organic acids. Other known examples of organic acids include, but are not limited to, alcohols, thiols, enols, phenols, and sulfonic acids. Organic acids may be monoprotic or polyprotic (e.g., diprotic, triprotic, etc.)

As used herein, an "organic base" is an organic compound with basic properties (i.e., it can function as a proton acceptor/sink). Many, but not all, organic bases contain nitrogen atoms (e.g., amines), and non-limiting examples of organic bases include amino acids (e.g., histidine, arginine, lysine), pyridine, imidazole and tromethamine. Organic bases may accept one or more protons per molecule.

"Charge profile," "charge state," "ionization," "ionization state," and "ionization profile" may be used interchangeably and refer to the ionization state due to protonation and/or deprotonation of the peptide's ionogenic groups.

As used herein, a "co-formulation" is a formulation that contains two or more therapeutic agents dissolved in an aprotic polar solvent system. The therapeutic agents may belong to the same class (for example, a co-formulation comprising two or more therapeutic peptides, such as insulin and pramlintide, or glucagon and GLP-1), or the therapeutic agents may belong to different classes (for example a co-formulation comprising one or more therapeutic small molecules and one or more therapeutic peptide molecules, such as GLP-1 and lisofylline).

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF THE INVENTION

Figure 1:
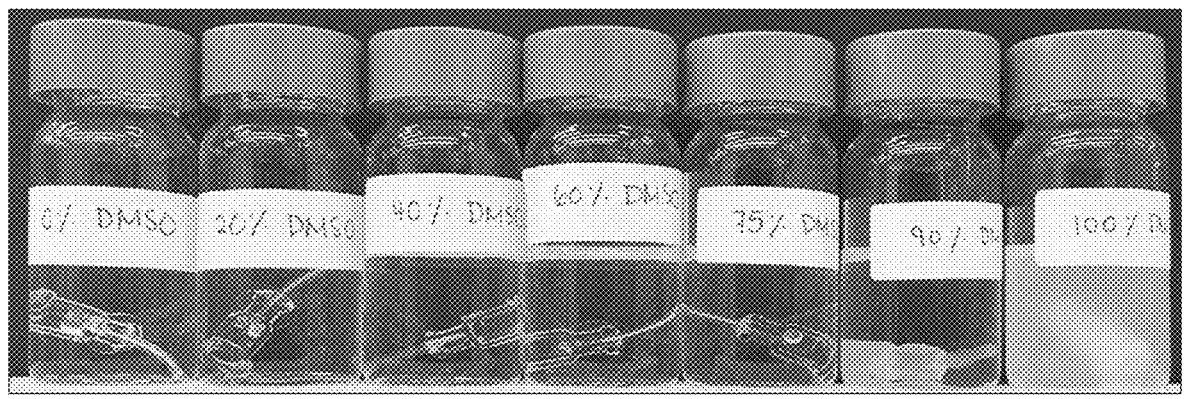
FIG. 1 shows the effect of the moisture content (% v/v) on a polycarbonate clear plastic Luer-type fitting from a commercially available infusion set. The moisture content is provided as (100%—DMSO content), with the DMSO content provided on each vial label. For example, for the sample listed as 60% DMSO, the moisture content is approximately 40% (v/v). Samples were photographed following 1 week at 45° C. in an incubating orbital shaker. In 0% moisture (100% DMSO) the plastic component partially dissolved in the solution, while at 10% moisture (90% DMSO) the clear plastic turned opaque, though did not appear to dissolve. At 25% moisture and above, the plastic component remained visibly clear and undissolved at the end of the storage period.

When prepared as aqueous solutions, standard small molecule, peptide, and protein molecules may be susceptible to multiple physical and chemical degradative pathways. For many of these therapeutic molecules, degradation pathways that are catalyzed, mediated and/or promoted by water (e.g., hydrolysis, racemization, deamidation) cannot be avoided and consequently the molecule cannot be adequately stabilized. Accordingly, many therapeutic agents cannot be prepared as stable solutions for parenteral injection and are instead prepared as powders that are reconstituted immediately prior to use.

To address the physical and/or chemical instability that many therapeutic molecules exhibit in water, formulations may be prepared wherein the therapeutic agent is dissolved in a biocompatible non-aqueous liquid, such as an aprotic polar solvent (e.g. DMSO). Previous non-aqueous formulations are at least partially based on the premise that limiting the moisture content of the formulation promotes physical and chemical stability by inhibiting water-mediated degradation pathways. Many of these known formulations limit the moisture content to at most 10% (w/w).

The use of aprotic polar solvents to prepare non-aqueous therapeutic formulations to inhibit many common degradation pathways, particularly those involving water, can significantly improve the stability of the solubilized or dissolved therapeutic molecule(s). However, problems still remain with the compositions and methods disclosed in the art. In particular, direct dissolution of a therapeutic molecule in an aprotic polar solvent is not a suitable approach for preparing stable compositions of most therapeutic molecules. Various therapeutics when solubilized directly in DMSO, for example glucagon at a concentration of 5 mg/mL, will form insoluble aggregates within one day of storage at room temperature. For a composition comprising only glucagon and DMSO, 5 mg/mL corresponds to approximately 0.45% (w/w) of the peptide compound, indicating that at even relatively low concentrations, direct dissolution in an aprotic polar solvent system is by itself incapable of preventing physical aggregation and/or gelation of a therapeutic molecule. Moreover, therapeutic molecules that may not form insoluble aggregates in an aprotic polar solvent system may nonetheless be prone to chemical degradation when solubilized directly in an aprotic polar solvent system.

Without wishing to be bound by theory, it is thought that in order to exhibit enhanced or optimal stability and solubility when formulated in an aprotic polar solvent system, a therapeutic molecule may require a specific ionization profile. The ionization profile is the charge state acquired via protonation and/or deprotonation of the therapeutic molecule's ionogenic groups. For example, protonation of the ionogenic amino acid residues (e.g., arginine, lysine, aspartic acid, glutamic acid) comprising a therapeutic peptide may confer an overall positive charge on the molecules in solution. Alternatively, deprotonation of ionogenic amino acid residues may confer an overall negative charge on the molecules in solution. For the non-limiting examples used herein, protonated (i.e., positively charged) molecules will be described, although the deprotonation of ionogenic amino acid residues in therapeutic peptide molecules is also considered to be within the scope of the present invention. The relatively long-range electrostatic repulsions between positively charged peptide molecules may inhibit the short-range hydrophobic interactions that can result in physical aggregation and/or gelation. Thus, in the absence of sufficient protonation (i.e., an optimal or beneficial ionization profile), therapeutic molecules dissolved in an aprotic polar solvent system may be physically unstable and lead to the formation of soluble and/or insoluble aggregates. Accordingly, it may be necessary to include at least one excipient in a sufficient concentration to function as an ionization stabilizing agent that is capable of imparting the ionization profile for improved physical and/or chemical stability to the active agent in the aprotic polar solvent system. The appropriate concentration of the ionization stabilizing excipient(s) to be added to the a solution depends on several factors including, but not limited to, the chemical structure of the ionization stabilizing excipient, the chemical structure of the active agent(s), the concentration of the active(s), the solvent system used, the presence of co-solvents, and the presence of additional excipients or formulation components and their respective concentrations.

Certain compositions and methods are designed to establish an optimal ionization profile for therapeutic molecules before they are solubilized in an aprotic polar solvent system. For example, a peptide powder from a supplier/manufacturer is initially dissolved in a buffered aqueous solution where the pH of the buffered aqueous peptide solution is set to that of optimal stability and solubility for the specific peptide. The peptide is then dried (for example via freeze drying or spray drying) to a powder from the aqueous solution such that the ionization profile of the peptide molecule in the powder may be about equal to the ionization profile of the peptide molecule in the aqueous solution from which it was dried. When the peptide powder is then solubilized in an aprotic polar solvent system, the ionization profile of the peptide molecule may be about equal to the ionization profile of the peptide molecule in the powder. Accordingly, the ionization profile of the peptide molecule in the aprotic polar solvent system is about equal to the ionization profile of the peptide molecule in the buffered aqueous solution.

The requirement for drying a therapeutic molecule from a buffered aqueous solution in order to optimize the ionization profile of the molecule and impart pH memory before it is solubilized in an aprotic polar solvent often imposes significant added costs, both in terms of time and expense, to the formulation development pathway. In particular, the drying process is well known to impose several stresses on the therapeutic molecule, and additional excipients (e.g., lyoprotectants such as trehalose and sucrose, and/or surfactants such as polysorbate 80) must be included in the aqueous solution in sufficient amounts to protect the therapeutic molecule, thereby increasing the cost and complexity of the formulation. Further, the drying process (e.g., spray drying, freeze drying) must often be optimized for a given therapeutic molecule, both at the lab-scale during initial research and development where the process is initially developed, and then during the manufacturing-scale as the process is scaled-up and transferred to instruments and facilities capable of producing commercial-scale batches. Consequently, the combination of initially developing and optimizing a drying process for a given therapeutic molecule, coupled with the time and costs associated with both transferring the method and incorporating an additional step in the manufacturing process can be very expensive. Without wishing to be bound by theory, it is believed that by providing a sufficient quantity of at least one ionization stabilizing excipient to achieve an appropriate or optimal ionization profile of the therapeutic molecule, electrostatic repulsion between therapeutic molecules possessing the same charge polarity (i.e. negatively or positively charged) may be sufficient in magnitude to prevent physical degradation (e.g., via short-range hydrophobic interaction between molecules that lead to aggregation). This is especially important for molecules that exhibit a tendency to aggregate in solution, particularly as the concentration of the molecule in solution is increased. Further, by controlling and optimizing the extent of the ionization (i.e., protonation or deprotonation) of the therapeutic agent, chemical degradation can be minimized, as, for example, an excess of protonation may promote chemical instability via degradative reactions such as oxidation (for example, oxidation of methionine residues) and fragmentation (for example, cleavage of the peptide backbone). Accordingly, for some therapeutic molecules, there may be an optimal or beneficial ionization profile achieved via protonation or deprotonation such that physical and/or chemical degradation reactions are minimized. For a therapeutic peptide, the extent of ionization (i.e., protonation or deprotonation) required for stability, and thus the amount of the ionization stabilizing excipient required in the solution, will depend on, among other things, the primary structure (i.e., amino acid sequence) and the peptide concentration in the solution.

Each molecule that functions as an ionization stabilizing excipient will exhibit a certain tendency to donate protons to, or accept protons from, the therapeutic molecule(s) and/or additional drug substance/powder components (e.g., salts, counterions, buffer molecules, etc.) in a given solvent system; the tendency to donate protons may be referred to as the relative acidic strength of the molecule, while the tendency to accept protons may be referred to as the relative basic strength of the molecule. As a non-limiting example, for a fixed concentration of a proton-donating molecule, (and for simplicity it is assumed only monoprotic molecules in this example) molecules that have a greater acidic strength will protonate the therapeutic molecule to a greater extent than a weaker acid. Accordingly, the concentration of a given proton-donating molecule (ionization stabilizing excipient) required to achieve an appropriate or optimal ionization profile for the therapeutic molecules will be inversely proportional to its acidic strength. These and other non-limiting aspects of the present invention are discussed herein.

In certain aspects, the aprotic polar solvent can be deoxygenated prior to preparation of the formulation. Many different techniques can be used in the context of the present invention to deoxygenate or remove oxygen from aprotic polar solvents (degasification or deoxygenation). For instance, it is contemplated that deoxygenation can, but is not limited to, remove oxygen that is dissolved in a liquid aprotic polar solvent either by the liquid alone, by the liquid and other solute molecules (e.g., micelles, cyclodextrins, etc.), or by other solute molecules alone. Non-limiting examples of deoxygenation techniques include placing the aprotic polar solvent under reduced pressure and/or heating the liquid to decrease the solubility of dissolved gas, fractional distillation, membrane degasification, substitution by inert gas, using a reducing agent, freeze-pump-thaw cycling, or long time storage in a container with air-locks. In one embodiment, the aprotic polar solvent is deoxygenated by vacuum degasification. In another embodiment the aprotic polar solvent is deoxygenated by using a deaerator. In one instance, the deaerator is a tray-type or cascade type deaerator. In another instance, the deaerator is a spray-type deaerator. In yet another embodiment, the aprotic polar solvent is deoxygenated using a gas-liquid separation membrane. In one instance, the aprotic polar solvent is degassed using a gas-liquid separation membrane and reduced pressure. In one embodiment, a non-oxygen gas (e.g., $N_2$) is bubbled through the liquid to replace or reduce oxygen in the aprotic polar solvent. In one instance, the gas bubbled through the aprotic polar solvent is argon, helium, nitrogen, an inert gas, and/or hydrogen gas, preferably nitrogen gas. In another instance, the gas is bubbled through the aprotic polar solvent using a gas-stripping column. In yet another embodiment, the aprotic polar solvent is deoxygenated by one or more reducing agent(s). Non-limiting examples of reducing agents include ammonium sulfite, hydrogen gas, active deoxygenating metals, copper, tin, cadmium, Wood's metal alloy (50% bismuth, 25% lead, 12.5% tin, and 12.5% cadmium), etc. In yet another embodiment, the aprotic polar solvent is degassed by freeze-pump-thaw cycling (e.g., at least 1, 2, 3, or more cycles can be used). In one instance, the freeze-pump-thaw cycle comprises freezing the aprotic polar solvent under liquid nitrogen, applying a vacuum, and then thawing the solvent in warm water. In one embodiment, the aprotic polar solvent is deoxygenated by long time storage in a steel, glass, or wood container. In another embodiment, the aprotic polar solvent is sonicated, ultrasonicated, or stirred during deoxygenation.

Once treated or deoxygenated, the aprotic polar solvents may have less than 0.1 mM of dissolved oxygen, preferably less than 0.05 mM of dissolved oxygen. Methods known to those of skill in the art can be used to determine the amount of dissolved oxygen in any given aprotic polar solvent (e.g., a dissolved oxygen meter or probe device can be used such as the Dissolved Oxygen Probe commercially available by Vernier (Beaverton, Oreg., USA)).

In certain aspects, the formulations disclosed in the present application can be prepared and/or sealed under an inert gas atmosphere. Common methods include backfilling the primary container-closure system (e.g., vials) to provide an inert gas (e.g., nitrogen, argon) headspace. A secondary container-closure system (e.g. sealed foil pouches) may also be sealed under an inert gas environment.

I. Formulations

Formulations of the present invention include a therapeutic agent present in an aprotic polar solvent system containing at least one ionization stabilizing excipient that is compatible with the container and/or fluid flow path. The therapeutic agent can be dissolved (e.g., fully or partially solubilized) or suspended (fully or partially) in the aprotic polar solvent system having an increased level of moisture.

In some embodiments, the therapeutic agent is present in an aprotic polar solvent that is "neat," i.e., that does not contain a co-solvent other than water. In other embodiments, the therapeutic agent is present in a solvent system that is a mixture of two or more aprotic polar solvents and a moisture or water content greater than 10% v/v (i.e., an aprotic polar solvent system). An example would be a 75/25 (% v/v) mixture of DMSO and NMP with a total moisture content of greater than 10% (v/v). In some embodiments, however, a co-solvent can be used, where in one or more aprotic polar solvents are mixed with a co-solvent. Non-limiting examples of co-solvents include (explicitly excluding water) ethanol, propylene glycol (PG), glycerol, and mixtures thereof. The co-solvent may be present in the formulation in an amount ranging from about 0.1% (w/v) to about 50% (w/v), e.g., about 0.1%, about 0.5%, about 1%, about 5%, about 10%, about 15%, about 20%, about 25%, about 30%, about 35%, or about 40% (w/v). In some embodiments, the co-solvent is present in the formulation in an amount ranging from about 10% (w/v) to about 50% (w/v), from about 10% (w/v) to about 40% (w/v), from about 10% (w/v) to about 30% (w/v), from about 10% (w/v) to about 25% (w/v), from about 15% (w/v) to about 50% (w/v), from about 15% (w/v) to about 40% (w/v), from about 15% (w/v) to about 30% (w/v), or from about 15% (w/v) to about 25% (w/v).

Still further, the formulations of the present invention can include one or more other excipients in addition to the (at least one) ionization stabilizing excipient. In some embodiments, the other excipient is selected from sugars, salts, starches, sugar alcohols, antioxidants, chelators, and preservatives. Examples of suitable sugars excipients include, but are not limited to trehalose, glucose, sucrose, etc. Examples of suitable starches for stabilizing excipients include, but are not limited to, hydroxyethyl starch (HES). Examples of suitable sugar alcohols (also referred to as polyols) for stabilizing excipients include, but are not limited to, mannitol and sorbitol. Examples of suitable antioxidants include, but are not limited to, ascorbic acid, cysteine, methionine, monothioglycerol, sodium thiosulphate, sulfites, BHT, BHA, ascorbyl palmitate, propyl gallate, N-acetyl-L-cysteine (NAC), and Vitamin E. Examples of suitable chelators include, but are not limited to, EDTA, EDTA disodium salt (edetate disodium), tartaric acid and salts thereof, glycerin, and citric acid and salts thereof. Examples of suitable inorganic salts include, but are not limited to, sodium chloride, potassium chloride, calcium chloride, magnesium chloride, calcium sulfate, magnesium sulfate, zinc sulfate and zinc acetate. Examples of suitable preservatives include, but are not limited to, benzyl alcohols, methyl parabens, metacresol, propyl parabens, and mixtures thereof. Additional formulation components include local anesthetics, such as lidocaine or procaine. In some embodiments, the additional stabilizing excipient is present in the formulation in an amount ranging from about 0.01% (w/v) to about 60% (w/v), from about 1% (w/v) to about 50% (w/v), from about 1% (w/v) to about 40% (w/v), from about 1% (w/v) to about 30% (w/v), from about 1% (w/v) to about 20% (w/v), from about 5% (w/v) to about 60% (w/v), from about 5% (w/v) to about 50% (w/v), from about 5% (w/v) to about 40% (w/v), from about 5% (w/v) to about 30% (w/v), from about 5%

(w/v) to about 20% (w/v), from about 10% (w/v) to about 60% (w/v), from about 10% (w/v) to about 50% (w/v), from about 10% (w/v) to about 40% (w/v), from about 10% (w/v) to about 30% (w/v), or from about 10% (w/v) to about 20% (w/v). In some embodiments, the additional stabilizing excipient is present in the formulation in an amount that is about, at most, or at least 0.01, 0.1, 0.5, 1, 2, 3, 4, 5, 6, 7, 8, 9, 10, 15, 20, 25, 30, 35, 40, 45, 50, 55, or 60% (w/v).

II. Therapeutic Agents

Therapeutic agents in the context of the present invention encompass peptide or protein compounds, small molecule drugs, and pharmaceutically acceptable analogs and/or salts thereof. One of skill is aware of which therapeutic agent is suitable for treating certain diseases or conditions and would be capable of administering effective amounts of a therapeutic agent in a formulation as described herein for the treatment of a disease or condition.

Non-limiting examples of peptides and proteins (and salts thereof) that can be used in the context of the present invention include, but are not limited to, glucagon, pramlintide, insulin, leuprolide, an luteinizing-hormone-releasing hormone (LHRH) agonist, parathyroid hormone (PTH), amylin, angiotensin(1-7), botulinum toxin, hematide, an amyloid peptide, gastric inhibitory peptide, an antibody (which may be monoclonal or polyclonal) or a fragment thereof, an immunogenic peptide (e.g., a peptide or peptide complex derived from a virus, a bacterium, or any prokaryotic or eukaryotic organism or cell thereof), an insulin-like growth factor, growth hormone releasing factor, anti-microbial factor, glatiramer, glucagon-like peptide-1 (GLP-1), a GLP-1 agonist, exenatide, analogs thereof, an amylin analog (pramlintide), and mixtures thereof. In some preferred aspects, the therapeutic agent is glucagon, insulin and/or pramlintide. Additional suitable examples of such peptides, proteins, peptide complexes and derivatives thereof that may be advantageously used in the compositions and methods of the present invention will be familiar to the ordinarily skilled artisan based on information that is provided herein and that is readily available in the art.

Non-limiting examples of small molecule drugs (and salts thereof) that can be used in the context of the present invention include, but are not limited to, epinephrine, benzodiazepines, levothyroxine, catecholemines, "triptans," sumatriptan, novantrone, chemotherapy small molecules (e.g., mitoxantrone), corticosteroid small molecules (e.g., methylprednisolone, beclomethasone dipropionate), immunosuppressive small molecules (e.g., azathioprine, cladribine, cyclophosphamide monohydrate, methotrexate), anti-inflammatory small molecules (e.g., salicylic acid, acetylsalicylic acid, lisofylline, diflunisal, choline magnesium trisalicylate, salicylate, benorylate, flufenamic acid, mefenamic acid, meclofenamic acid, triflumic acid, diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin, sulindac, phenylbutazone, oxyphenbutazone, azapropazone, feprazone, piroxicam, isoxicam), small molecules used to treat neurological disorders (e.g., cimetidine, ranitidine, famotidine, nizatidine, tacrine, metrifonate, rivastigmine, selegilene, imipramine, fluoxetine, olanzapine, sertindole, risperidone, valproate semisodium, gabapentin, carbamazepine, topiramate, phenytoin), small molecules used to treat cancer (e.g., vincristine, vinblastine, paclitaxel, docetaxel, cisplatin, irinotecan, topotecan, gemcitabine, temozolomide, imatinib, bortezomib), statins (e.g., atorvastatin, amlodipine, rosuvastatin, sitagliptin, simvastatin, fluvastatin, pitavastatin, lovastatin, pravastatin, simvastatin), and other taxane derivatives, small molecules used to treat tuberculosis (e.g., rifampicin), small molecule anti-fungal agents (e.g., fluconazole), small molecule anti-anxiety agents and small molecule anti-convulsant agents (e.g., lorazepam), small molecule anti-cholinergic agents (e.g., atropine), small molecule β-agonist drugs (e.g., albuterol sulfate), small molecule mast cell stabilizers and small molecule agents used to treat allergies (e.g., cromolyn sodium), small molecule anesthetic agents and small molecule anti-arrhythmic agents (e.g., lidocaine), small molecule antibiotic agents (e.g., tobramycin, ciprofloxacin), small molecule anti-migraine agents (e.g., sumatriptan), and small molecule anti-histamine drugs (e.g., diphenhydramine). In preferred embodiments, the small molecule is epinephrine.

The therapeutic agent of the invention can be administered intracutaneously in the prevention, diagnosis, alleviation, treatment, or cure of disease. Examples of proteins and proteinaceous compounds which may be formulated and employed in the delivery system according to the present invention include those proteins which have biological activity or which may be used to treat a disease or other pathological conditions.

Each of the aforementioned peptides, proteins, and small molecule drugs are well-known and commercially available from a variety of manufacturers and sources. Further, the amount of the peptides, proteins, or small molecule drugs in the dosage formulations can be varied depending on currently acceptable amounts, subject/patient needs (e.g., age, health, weight, nature and extend of symptom), and the like; such amounts are readily determined by one of ordinary skill in the pharmaceutical and pharmacological arts based on information that is readily available.

The therapeutic agents provided by the manufacturer or commercial source are typically provided in a powdered form for dissolution into the formulations as described herein. A number of known techniques can be used to form a powdered agent for dissolution.

Any suitable dosage of peptide or peptides can be formulated in the stable formulations of the present invention. Generally, the peptide (or, in embodiments comprising two or more peptides, each of the peptides) is present in the formulation in an amount ranging from about 0.1 mg/mL up to the solubility limit of the peptide or peptides. In certain such embodiments, the dosage is from about 0.1 mg/mL to about 500 mg/mL, or up to about 200 mg/mL, about 250 mg/mL, about 300 mg/mL, about 350 mg/mL, about 400 mg/mL, about 450 mg/mL or about 500 mg/mL. In some embodiments, the peptide is present in the formulation in an amount ranging from about 2 mg/mL to about 60 mg/mL. In other embodiments, the peptide is present in the formulation in an amount ranging from about 3 mg/mL to about 50 mg/mL. In still other embodiments, the peptide is present in the formulation in an amount ranging from about 5 mg/mL to about 15 mg/mL. In yet other embodiments, the peptide is present in the formulation in an amount ranging from about 0.1 mg/mL to about 10 mg/mL (e.g., about 0.5 mg/mL, about 1 mg/mL, about 2 mg/mL, about 2.5 mg/mL, about 3 mg/mL, about 4 mg/mL or about 5 mg/mL). In yet other embodiments, the peptide is present in the formulation in an amount ranging from about 1 mg/mL to about 50 mg/mL. Again, it will be readily apparent to those of skill that the peptide dosage can be varied depending on the peptide used and the disease, disorder or condition to be treated, based on information provided herein and that is readily available in the relevant arts.

In some embodiments, the formulations of the present invention further comprise an antioxidant. In other embodiments, the formulations further comprise a chelator. In still other embodiments, the formulations of the present invention further comprise a preservative, sugar (e.g., a monosaccharide, a disaccharide or a polysaccharide), a sugar alcohol, a polyol, a surfactant and/or a salt.

III. Therapeutic Methods

In another aspect, the present invention provides methods of treating diseases, conditions, or disorders by administering to a subject a therapeutic agent for treating a disease, condition, or disorder in a stable formulation as described herein in an amount effective to treat, alleviate, or prevent the disease, condition, or disorder.

In some embodiments, a therapeutic method of the present invention comprises treating hypoglycemia by administering to a subject having hypoglycemia a therapeutic agent for hypoglycemia in a stable formulation as described herein in an amount effective to treat the hypoglycemia. In some embodiments, the subject is administered a stable formulation comprising glucagon. In certain aspects, hypoglycemia can be caused by diabetes or non-diabetes related diseases, conditions, and disorders.

As described by the Workgroup of the American Diabetes Association and the Endocrine Society, (Seaquist, et al, (2013), *Diabetes Care*, Vol 36, pages 1384-1395) with respect to hypoglycemia a single threshold value for plasma glucose concentration that defines hypoglycemia in diabetes is not typically assigned because glycemic thresholds for symptoms of hypoglycemia (among other responses) shift to lower plasma glucose concentrations after recent antecedent hypoglycemia and to higher plasma glucose concentrations in patients with poorly controlled diabetes and infrequent hypoglycemia.

Nonetheless, an alert value can be defined that draws the attention of both patients and caregivers to the potential harm associated with hypoglycemia. Patients at risk for hypoglycemia (i.e., those treated with a sulfonylurea, glinide, or insulin) should be alert to the possibility of developing hypoglycemia at a self-monitored plasma glucose—or continuous glucose monitoring subcutaneous glucose—concentration of ≤70 mg/dL (≤3.9 mmol/L). Because it is higher than the glycemic threshold for symptoms in both nondiabetic individuals and those with well-controlled diabetes, it generally allows time to prevent a clinical hypoglycemic episode and provides some margin for the limited accuracy of monitoring device at low-glucose levels.

The condition of severe hypoglycemia is an event requiring assistance of another person to actively administer carbohydrates, glucagon, or take other corrective actions. Plasma glucose concentrations may not be available during an event, but neurological recovery following the return of plasma glucose to normal is considered sufficient evidence that the event was induced by a low plasma glucose concentration. Typically, these events begin occurring at plasma glucose concentrations of ≤50 mg/dL (2.8 mmol/L). Documented symptomatic hypoglycemia is an event during which typical symptoms of hypoglycemia are accompanied by a measured plasma glucose concentration ≤70 mg/dL (≤3.9 mmol/L). Asymptomatic hypoglycemia is an event not accompanied by typical symptoms of hypoglycemia but with a measured plasma glucose concentration ≤70 mg/dL (≤3.9 mmol/L). Probable symptomatic hypoglycemia is an event during which symptoms typical of hypoglycemia are not accompanied by a plasma glucose determination but that was presumably caused by a plasma glucose concentration ≤70 mg/dL (≤3.9 mmol/L). Pseudo-hypoglycemia is an event during which the person with diabetes reports any of the typical symptoms of hypoglycemia with a measured plasma glucose concentration >70 mg/dL (>3.9 mmol/L) but approaching that level.

Further included in the indications which may be treated by the disclosed invention are hypoglycemia-associated autonomic failure (HAAF). As described by Philip E. Cryer, Perspectives in Diabetes, Mechanisms of Hypoglycemia-Associated Autonomic Failure and Its Component Syndromes in Diabetes, Diabetes, Vol. 54, pp. 3592-3601 (2005), "recent antecedent iatrogenic hypoglycemia causes both defective glucose counter-regulation (by reducing epinephrine responses to a given level of subsequent hypoglycemia in the setting of absent decrements in insulin and absent increments in glucagon) and hypoglycemia unawareness (by reducing sympathoadrenal and the resulting neurogenic symptom responses to a given level of subsequent hypoglycemia) and thus a vicious cycle of hypoglycemia." HAAF affects those with type 1 and advanced type 2 diabetes. Additionally, the invention of the present disclosure may also treat hypoglycemia in patients following islet cell transplantation.

The formulations of the present invention can also be used for the treatment of hyperinsulinemic hypoglycemia, which broadly refers to the condition and effects of low blood glucose levels that are caused by excessive insulin. The most common type of severe, but typically transient, hyperinsulinemic hypoglycemia arises from the administration of exogenous insulin in patients with Type 1 diabetes. This type of hypoglycemia can be defined as iatrogenic hypoglycemia and is a limiting factor in the glycemic management of type 1 and type 2 diabetes. Nocturnal hypoglycemia (night-time hypo) is a common type of iatrogenic hypoglycemia arising in patients taking exogenous insulin. However, hyperinsulinemic hypoglycemia can also arise due to endogenous insulin, for example in congenital hyperinsulinism, insulinomas (insulin-secreting tumors), exercise-induced hypoglycemia and reactive hypoglycemia. Reactive hypoglycemia is a non-diabetic hypoglycemia and is due to low blood sugar that occurs following a meal—typically within four hours after eating. Reactive hypoglycemia may also be referred to as postprandial hypoglycemia. Symptoms and signs of reactive hypoglycemia can include hunger, weakness, shakiness, sleepiness, sweating, confusion and anxiety. Stomach surgery (e.g., bariatric surgery) is one possible cause, as following surgery food may pass too quickly into the small intestine (e.g., post-bariatric hypoglycemia (PBH)). Additional causes include enzyme deficiencies that make it difficult for the body to breakdown food, or increased sensitivity to the hormone epinephrine.

In some embodiments, the disease, condition, or disorder to be treated with a stable formulation of the present invention is a diabetic condition. Examples of diabetic conditions include, but are not limited to, type 1 diabetes, type 2 diabetes, gestational diabetes, pre-diabetes, hyperglycemia, hypoglycemia, and metabolic syndrome. In some embodiments, the disease, condition, or disorder is hypoglycemia, including but not limited to diabetes-related hypoglycemia, exercise-induced hypoglycemia, and post-bariatric surgery hypoglycemia, or other types of hypoglycemia described herein and known to those of ordinary skill in the art. In some embodiments, the disease, condition, or disorder is diabetes.

In some embodiments, a therapeutic method of the present invention comprises treating diabetes by administering to a subject having diabetes a therapeutic agent in a stable formulation as described herein in an amount effective to treat the diabetes. In some embodiments, the subject is administered a stable formulation comprising insulin. In some embodiments, the subject is administered a stable formulation comprising pramlintide. In some embodiments, the subject is administered a stable formulation comprising insulin and pramlintide. In some embodiments, the subject is administered a stable formulation comprising exenatide. In some embodiments, the subject is administered a stable formulation comprising glucagon and exenatide.

In certain aspects, epinephrine can be administered to a subject at risk of or suspected of anaphylaxis. Epinephrine is indicated as an emergency treatment of Type I allergic reactions which can arise from multiple sources, including, but not limited to, foods, drugs and/or other allergens, allergen immunotherapy, diagnostic testing substances, insect stings and bites, and idiopathic or exercise-induced anaphylaxis.

Administered dosages for the peptide or small molecule drugs as described herein for treating a disease, condition, or disorder (e.g., a diabetic condition, hypoglycemia, or anaphylaxis) are in accordance with dosages and scheduling regimens practiced by those of skill in the art. General guidance for appropriate dosages of all pharmacological agents used in the present methods is provided in Goodman and Gilman's, The Pharmacological Basis of Therapeutics, 11th Edition, 2006, supra, and in the Physicians' Desk Reference (PDR), for example, in the 65th (2011) or 66th (2012) Eds., PDR Network, LLC, each of which is hereby incorporated herein by reference. The appropriate dosage of a peptide drug for treating a disease, condition, or disorder as described herein will vary according to several factors, including the formulation of the composition, patient response, the severity of the condition, the subject's weight, and the judgment of the prescribing physician. Effective doses of the described formulations deliver a medically effective amount of a peptide drug. The dosage can be increased or decreased over time, as required by an individual patient or determined by medical personnel.

Determination of an effective amount or dose is well within the capability of those skilled in the art, especially in light of the detailed disclosure provided herein. Generally, the formulations to deliver these doses may contain one, two, three, four, or more small molecules, peptides, or peptide analogs (collectively "peptide," unless peptide analogs are expressly excluded), wherein each peptide is present at a concentration from about 0.1 mg/mL up to the solubility limit of the peptide in the formulation. This concentration is preferably from about 1 mg/mL to about 100 mg/mL. In certain aspects, the concentration is about 1 mg/mL, about 2 mg/mL, about 2.5 mg/mL, about 3 mg/mL, about 4 mg/mL, about 5 mg/mL, about 7.5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL. The concentrations for small molecules are known to medical personnel and can be established and implemented using the disclosure provided herein, e.g., 0.01 mg/ml to 500 mg/ml, or in doses of about 1, 2, 2.5, 3, 4, 5, 10, 25, 50, 75, 100, 200, 500, to about 1000 mg, including all values and ranges there between.

The formulations of the present invention may be used for parenteral administration, including, but not limited to, subcutaneous, intradermal, intramuscular, intranasal, buccal, transdermal or intravenous administration (e.g., by injection or by infusion). In some embodiments, the formulation is administered subcutaneously. The formulations can also be delivered transdermally, such as by topically applying the composition to skin (e.g., spreading the composition on skin or loading the composition onto a dermal patch and attaching the dermal patch to the skin).

The formulations of the present disclosure can be administered by infusion or by injection using any suitable device. For example, a formulation of the present invention may be placed into a syringe (e.g., a pre-filled syringe), a pen injection device, an auto-injector device, or a pump device. In some embodiments, the injection device is a multi-dose injector pump device or a multi-dose auto-injector device. The formulation is presented in the device in such a fashion that the formulation is readily able to flow out of the needle upon actuation of an injection device, such as an auto-injector, in order to deliver the peptide drugs. Suitable pen/auto injector devices include, but are not limited to, those pen/auto injection devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like.

In some embodiments, the formulations of the present invention are provided ready for administration in a vial, a cartridge, or a pre-filled syringe.

In some embodiments, the stable formulation is used for formulating a medicament for the treatment of hypoglycemia. In some embodiments, the stable formulation comprises glucagon or a salt thereof (e.g., glucagon acetate). In some embodiments, the stable formulation comprises glucagon and exenatide.

In some embodiments, the stable formulation is used for formulating a medicament for the treatment of diabetes. In some embodiments, the stable formulation comprises insulin. In some embodiments, the stable formulation comprises exenatide. In some embodiments, the stable formulation comprises pramlintide. In some embodiments, the stable formulation comprises insulin and pramlintide.

In additional embodiments, the formulations provided by the present invention may be used in certain diagnostic procedures. In particular such embodiments, a glucagon-containing formulation of the present invention can be administered to a mammal, such as a human or a veterinary animal, prior to, as an adjunct to, as a part of, or in conjunction with, one or more diagnostic procedures, thereby providing a method of diagnosing the disease or disorder in a patient suffering from or predisposed to the disease or disorder. Non-limiting examples of such diagnostic procedures in which a glucagon-containing formulation of the present invention may be suitably used include methods for diagnosing Alzheimer's Disease (see U.S. Pat. No. 4,727,041, incorporated herein by reference in its entirety) and growth hormone deficiency (see U.S. Pat. No. 5,065,747; see also Boguszewski, C. L., *Endocrine* 57: 361-363 (2017), and Yuen, K. C. J., *ISRN Endocrinology*, vol. 211, Article ID 608056, pp. 1-6 (2011), doi:10.5402/2011/608056; the disclosures of all of which are incorporated by reference herein in their entireties). Additional examples of such uses include in certain radiologic diagnostic procedures, particularly those used in diagnosing gastroenterologic conditions (non-limiting examples of which include abdominal obstructions, appendicitis, Barrett's esophagus, celiac disease, cancers, cirrhosis, Crohn's disease, diverticulitis, diverticulosis, ulcers, gallstones, gastric prolapse, gastritis, gastroesophageal reflux disease, hepatitis (A/B/C), hiatus hernia, inflammatory bowel disorder, hernia, irritable bowel syndrome, pancreatitis, perianal fissure, ulcerative colitis, and the like), during radiologic examinations of the gastrointestinal system to temporarily inhibit movement of the organs and connective tissues of the gastrointestinal tract in adult patients (see, e.g., product label for glucagon, lyophilized (NDC Code 63323-185-03), accessible at: https://dailymed.nlm.nih.gov/dailymed/drugInfo.cfm?setid=8c8acad6-44cc-43aa-966b-027e053be8f5; see also, *Glucagon in Gastroenterology*, J. Picazo, ed., Lancaster, England: MTP Press Ltd. (1979), especially Chapters 3-7, pp. 39-120; the disclosure of which is incorporated herein by reference). In such diagnostic methods, the glucagon-containing formulation of the invention is administered to the patient suffering from or predisposed to the disorder by any suitable method of introduction of such formulation into the body of the patient such as those described herein, e.g., intravenously at dosages of about 0.2 mg to about 0.75 mg about 1-10 minutes prior to the diagnostic test (e.g., the radiologic procedure), or intramuscularly or intradermally at dosages of about 1 mg to about 2 mg about 5-15 minutes prior to the diagnostic test (e.g., the radiologic procedure). Other suitable therapeutic and diagnostic methods of use of the formulations of the present invention will be readily familiar to the ordinarily skilled clinician or pharmacist based on the disclosure contained herein in view of information that is available in the art.

IV. Kits/Containers

Kits are also contemplated as being used in certain aspects of the present invention. For instance, a formulation of the present invention can be included within a kit, which can include a container. In one aspect, for instance, the formulation can be comprised within a container that is ready to administer to or be incorporated into a device configured to administer to a subject without having to reconstitute or dilute the formulation. That is, the formulation to be administered can be stored in the container and be readily used as needed. The container can be a device. The device can be a syringe (e.g., pre-filled syringe), a pen injection device, an auto-injector device, a device that can pump or administer the formulation (e.g., automatic or non-automatic external pumps (e.g., patch pumps, or pumps requiring an external infusion set), implantable pumps, etc.) or a perfusion bag. Suitable pen/auto-injector devices include, but are not limited to, those pen/auto-injection devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like. Suitable infusion sets include, but are not limited to, those manufactured/distributed/sold by Tandem Diabetes Care, Inc., Medtronic, Disetronic, YpsoMed Ag, Unomedical A/S and the like.

EXAMPLES

Some embodiments of the present disclosure will be described in greater detail by way of specific examples. The following examples are offered for illustrative purposes and are not intended to limit any present invention in any manner. For example, those of skill in the art will readily recognize a variety of noncritical parameters which can be changed or modified, without undue experimentation, to yield essentially the same results.

Example 1: Compatibility of Infusion Systems with DMSO-Containing Formulations

In an initial study of the compatibility of certain infusion systems/sets with DMSO-containing formulations and compositions of the invention, the hard-plastic portion (i.e., the pump connector) of a commercially available infusion set (Cleo, Ypsomed) was immersed in various mixtures of DMSO and water, ranging from 0% DMSO (pure water) to 100% DMSO (neat DMSO). Samples were photographed following 1 week at 45° C. in an incubating orbital shaker. Note that no additional formulation components (e.g., active ingredient) were included in this example.

FIG. 1 shows the effects of the DMSO content (% v/v) on the structural integrity of the infusion system connector—a measure of the compatibility of this component, and thus of the infusion system as a whole, with certain formulations of the present invention. The hard-plastic portion of the infusion set was made from polycarbonate, and was the only portion of the infusion set that was observed to be incompatible with DMSO when examined under real-world in-use conditions. At 75% (v/v) DMSO (i.e., 25% (v/v) water) or lower, the infusion set component was visually compatible with the solvent system (i.e., the plastic remained clear and undissolved). At 90% DMSO (i.e., 10% (v/v) water), the component exhibited discoloration (i.e., opaqueness), while in 100% DMSO the component began to dissolve with 10 minutes following immersion.

Figure 2:
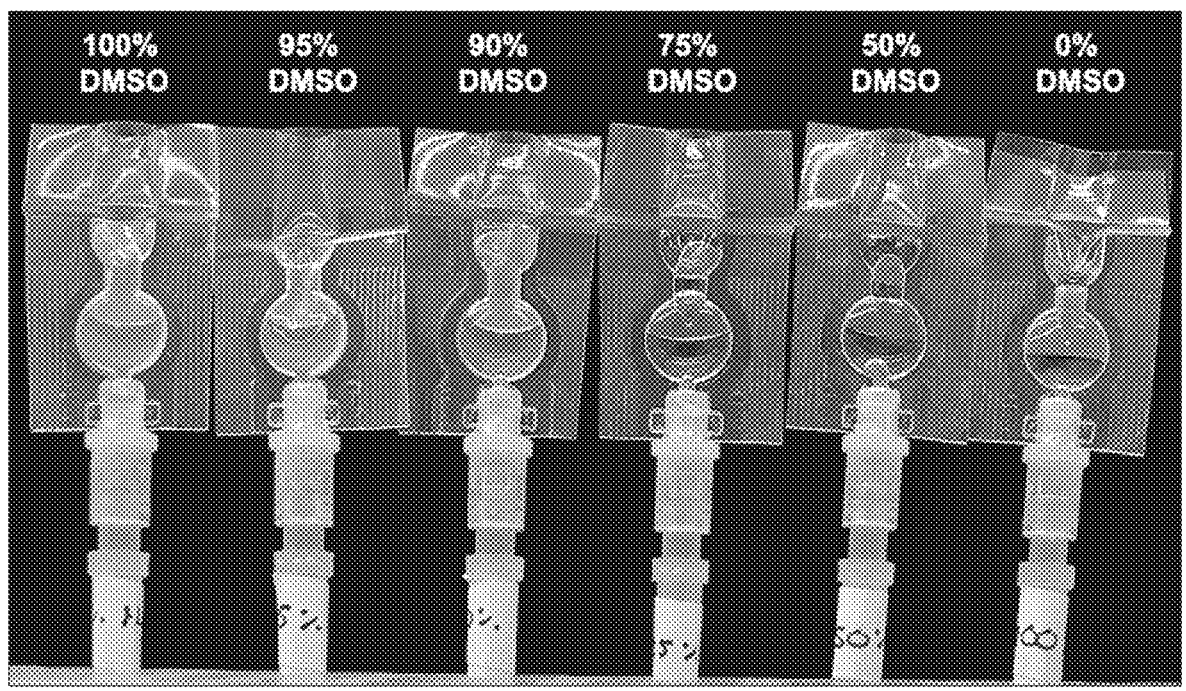
FIG. 2 shows the effect on a pre-fillable injection system (UniJect™; Becton-Dickenson) devices filled with DMSO-$H_2O$ mixtures following 2 weeks of storage at 45° C. The plastic was visibly opaque at 100%, 95% and 90% added moisture, and visibly clear at 25%, 50% and 100% added moisture.

The improved visual compatibility with DMSO-based solutions prepared with higher moisture content was further demonstrated with a different commercially available plastic-based delivery system: the UniJect™ injection system (Becton Dickinson). These pre-filled syringe devices are designed to be low-cost for use in third-world countries and are injection molded from a single piece of plastic. Initial stability studies (not shown) indicated that high DMSO-concentration formulations (i.e., >90% (v/v)) were not compatible with this injection system, with DMSO-based formulations promoting discoloration (opaqueness) and delamination of the plastic during accelerated storage. However, subsequent compatibility studies were performed using DMSO solutions having a range of added moisture content according to the present invention. In this study, UniJect™ devices were filled with DMSO-H$_2$O mixtures and were photographed following 2 weeks of storage at 45° C. As shown in FIG. 2, the UniJect™ devices were discolored and opaque in solutions containing 100%, 95% and 90% DMSO (note that these solutions contained 0%, 5% and 10% added moisture (v/v)). At 25% added moisture (or 75% DMSO), the plastic appeared clear, similar in appearance to the 100% water (or 0% DMSO) samples. In contrast, the plastic was visibly clear at 75%, 50% and 0% DMSO (corresponding to 25%, 50% and 100% added moisture, respectively).

Taken together, the results of these studies indicate that high moisture content (e.g., high water content) DMSO-containing formulations, particularly those formulations at 75% DMSO (v/v) concentration or below, are likely to be compatible with most, if not all, plastic-containing commercially available injection systems.

Example 2: Storage Stability of Glucagon in High Moisture Content Formulations

Based on the results described in Example 1, it was of interest to examine the stability of certain therapeutic compounds, e.g., glucagon, in high moisture content formulations, so as to enable the use of plastic-containing infusion systems with DMSO-based glucagon therapeutic formulations.

Stability studies with high moisture glucagon-based formulations indicated that additional acid will be required to inhibit physical instability (i.e., fibril formation and/or gelling) in the formulation. For a 5 mg/mL glucagon formulation, physical stability was observed to be related to the acid concentration added to the formulation. Glucagon formulations were prepared at 5 mg/mL in DMSO (with varying concentrations of water in the solution) in glass vials, having varying concentrations of a mineral acid (e.g., HCl or $H_2SO_4$; in the present study, HCl was used) also present in the solution. Following three weeks of storage of the glucagon formulations in glass vials at 45° C., the vials were examined visually for the presence of gelation or aggregation of the contents of the vial. Results of these studies are shown in Table 1, where the check mark indicates that the sample was physically stable (i.e., no visual observation of gelation or aggregation), and the 'X' indicates that gelling and/or aggregation was observed in the sample). These initial studies demonstrated that a physically stable glucagon formulation could be prepared having a high moisture content.

TABLE 1

Physical stability of 5 mg/mL glucagon formulations in varying moisture (water) content (v/v with DMSO) and mineral acid concentrations (3 mM-7 mM)

|  | 3 mM | 4 mM | 5 mM | 6 mM | 7 mM |
|---|---|---|---|---|---|
| 0% Moisture | ✓ | ✓ | ✓ | ✓ | ✓ |
| 10% Moisture | ✓ | ✓ | ✓ | ✓ | ✓ |
| 20% Moisture | X | ✓ | ✓ | ✓ | ✓ |
| 30% Moisture | X | X | ✓ | ✓ | ✓ |
| 40% Moisture | X | X | X | ✓ | ✓ |
| 50% Moisture | X | X | X | ✓ | ✓ |

Prior studies on the chemical stability of physically stable (i.e., non-gelling) formulations had indicated that the presence of high levels of moisture in DMSO/peptide (e.g., glucagon) formulations promotes chemical degradation of the peptide. As discussed in U.S. Pat. No. 9,649,364 (the disclosure of which is incorporated herein by reference in its entirety), the addition of an ionization stabilizing excipient (e.g., a proton donor) is required to inhibit gelling, with this stabilizing effect perhaps being due to the increased electrostatic repulsions between positively charged neighboring molecules, which inhibit the formation of the relatively shorter-range hydrophobic interactions (i.e., the alignment of hydrophobic regions of neighboring molecules) that are believed to promote fibrillation and gelling).

Without wishing to be bound by theory, it is thought that the addition of higher levels of moisture imparts multiple destabilizing effects to a DMSO-based peptide formulation. These include (but are not limited to) the following: (1) higher moisture content will promote the hydrophobic interactions (i.e. the higher moisture will drive the hydrophobic regions of neighboring molecules together) which results in gelling and fibrillation; and (2) higher moisture will begin to promote the destabilizing hydrolysis reactions (e.g., fragmentation, deamidation, and aspartic acid isomerization) that are responsible for the instability of aqueous-based formulations. The first pathway can be inhibited via the addition of more protons (i.e., acids, particularly mineral acids such as sulfuric acid, hydrochloric acid and/or nitric acid) through inclusion of an ionization stabilizing excipient (similar to that described in U.S. Pat. No. 9,649,364). It is believed that the increased proton concentration will enhance the strength of the electrostatic repulsions between neighboring peptide molecules. However, the addition of more protons also catalyzes many of the water-mediated degradation reactions, promoting chemical degradation of the peptide. Thus, as is known in the art, the addition of water to a peptide-containing solution can promote instability of the peptide. However, a formulation that exhibits acceptable long-term stability at low temperatures (i.e., refrigerated temperatures) may still be suitable for use in a pump-based product, where exposure to elevated temperature (e.g., 37° C.) is relatively brief (≤1 week).

Glucagon formulations containing varying water content and mineral acid concentrations were prepared and examined for both physical and chemical stability upon storage. Sample formulations were prepared by dissolving glucagon powder to a 5 mg/mL concentration in DMSO containing a moisture (water) content between 30-40% (v/v). Additionally, an acid concentration (HCl) range between 5-9 mM was included in the formulations to inhibit fibrillation/gelling and promote physical stability. The solutions were filled into 2 mL glass vials, stoppered and stored inverted in either a 5° C. or 25° C./60% RH stability chamber. Although pure DMSO has a freezing point of approximately 18.5° C., the high moisture content of the formulations depresses the freezing point such that the solutions do not solidify at 5° C. The physical and chemical stability of the formulations were evaluated following eight weeks (56 days) of storage. Physical stability was assessed visually (observing for formation of fibrils or gelation of the solution), while chemical stability was assessed by UHPLC-UV (280 nm) using a glucagon stability-indicating method (see U.S. Pat. No. 9,649,364).

At the eight-week time-point, visual inspection of all formulations revealed clear, colorless solutions that were visibly free of particulate matter. No fibrillation or gelling was observed in any of the samples.

Chemical stability results are shown in Table 2; data indicate the percent purity of the glucagon peak via UHPLC at the specified temperature (n=1 for each sample). These results indicate that at 5° C. the solutions (which did not freeze) exhibit excellent stability.

TABLE 2

Chemical Stability of High-Moisture Formulations of Glucagon Upon Storage

| Sample | 5° C. | 25° C. |
|---|---|---|
| 30% $H_2O$/5 mM HCl | 99.6% | 97.1% |
| 30% $H_2O$/7 mM HCl | 99.6% | 95.5% |
| 30% $H_2O$/9 mM HCl | 98.9% | 92.6% |
| 35% $H_2O$/5 mM HCl | 99.5% | 96.2% |
| 35% $H_2O$/7 mM HCl | 99.0% | 94.3% |
| 35% $H_2O$/9 mM HCl | 98.9% | 91.2% |
| 40% $H_2O$/5 mM HCl | 99.1% | 95.1% |
| 40% $H_2O$/7 mM HCl | 99.0% | 93.2% |
| 40% $H_2O$/9 mM HCl | 98.6% | 89.9% |

At 5° C., increasing moisture and acid content appeared to promote minor degradation of the glucagon peptide, although the difference in measured peak purity between all samples varied by ≤1%. At 25° C., the influence of acid and moisture was more pronounced, with both components promoting degradation. However, all formulations appeared to have acceptable physical and chemical stability for a 1-month in-use period at room temperature coupled with longer-term storage at refrigerated conditions.

To expand these studies and couple them with the information relating to infusion systems obtained in Example 1, three different 5 mg/mL glucagon formulations were prepared and evaluated upon introduction into a development-stage patch pump containing an internal plastic reservoir wherein the formulation was filled into the device. One low moisture ("Formulation 1") and two high moisture formulations ("Formulation 2" and "Formulation 3"). These formulations contained the components shown in Table 3. The moisture content of "Formulation 1" is <1.5% (v/v), while Formulations 2 and 3 were prepared at 35% (v/v) and 50% (v/v) moisture contents, respectively.

TABLE 3

Test Glucagon Formulations for Evaluation in Patch Pump Delivery System

|  | Formulation 1 | Formulation 2 | Formulation 3 |
| --- | --- | --- | --- |
| Active | 5 mg/mL Glucagon | 5 mg/mL Glucagon | 5 mg/mL Glucagon |
| Excipients | 5.53% (w/v) Trehalose DH | 35% (v/v) H2O | 50% (v/v) H2O |
|  | 2.9% (w/v) Mannitol | 7 mM $H_2SO_4$ | 8 mM $H_2SO_4$ |
|  | 3.2 mM $H_2SO_4$ | DMSO | DMSO |
|  | DMSO |  |  |

The plastic-based fluid reservoirs of separate pumps were filled with approximately 1.5 mL of each respective formulation and delivered over three days at a steady infusion rate of 500 µL (0.5 mL) per day. The pumps were placed in a 35° C. oven during the three-day delivery period to simulate body surface temperature when worn by a patient. For each injector, the delivered fluid was collected into a glass vial to be analyzed by UHPLC.

Within 30 minutes of filling the pumps with Formulation 1 (the low moisture formulation), there was a system error, indicating that the pumps were no longer operating. Examination of the pumps revealed that the formulation had leaked in the pump (i.e., it had caused an opening in the flow path by dissolving a plastic component of the reservoir). In contrast, pumps filled with both high-moisture formulations (2 and 3) functioned as expected over the three-day period, with no indication of leakage within the pump.

As a control, the samples were also stored in glass vials under the same conditions. For each formulation, three vials and two patch pump samples were examined. Results are shown in Table 4.

TABLE 4

Chemical Stability of Vialed and Pump (OnBody Injector) Samples of Glucagon/DMSO Formulations

| Storage Container | Excipients | % Purity |
| --- | --- | --- |
| Glass Vial | 35% H2O, 7 mM HCl | 98.4% |
| Glass Vial | 35% H2O, 7 mM HCl | 98.4% |
| Glass Vial | 35% H2O, 7 mM HCl | 98.3% |
| Pump | 35% H2O, 7 mM HCl | 98.7% |
| Pump | 35% H2O, 7 mM HCl | 98.8% |
| Glass Vial | 50% H2O, 8 mM HCl | 96.9% |
| Glass Vial | 50% H2O, 8 mM HCl | 97.0% |
| Glass Vial | 50% H2O, 8 mM HCl | 96.8% |
| Pump | 50% H2O, 8 mM HCl | 98.0% |
| Pump | 50% H2O, 8 mM HCl | 97.7% |

These results indicate that peptide stability is not negatively impacted by the flow contact path (e.g., plastic and rubber components) in the pumps, with both formulations exhibiting comparable stability between glass vials and pumps. The data demonstrates the viability of a high-moisture DMSO-based formulation for delivery via commercial pumps, while illustrating the incompatibility of high DMSO-content (>90% (w/w)) formulations with some pump-based delivery systems. Taken together, these studies indicate that high-moisture DMSO/glucagon formulations can be prepared that exhibit excellent long-term storage stability under refrigerated conditions coupled with high in-use stability and compatibility with commercial pumps.

Example 3: Long-Term Storage Stability of Glucagon in High Moisture Content Formulations To demonstrate the long-term storage stability of high-moisture glucagon formulations, DMSO-based peptide formulations were prepared containing between 30-50% (v/v) moisture. The concentration of glucagon was 5 mg/mL for all formulations evaluated. Sulfuric acid (either 6 mM or 7 mM) was included in the samples to maintain physical stability The samples were stored in 2R ISO glass vials at either 2-8° C. or −20° C. for over 1 year (398 days) and then characterized for physical and chemical stability. Physical stability was assessed by visually examining samples for indications of fibrillation, including formation of insoluble particulate matter and/or gelling. Chemical stability (i.e. glucagon peak purity) was examined using a stability-indicating UHPLC method as described in Example 2. Results are shown in Table 5.

TABLE 5

UHPLC Data (glucagon peak purity) for Samples Following 398 Days at Specified Storage Conditions (N = 1)

| Moisture | Temp = 2-8° C. [$H_2SO_4$] | | Temp = −20° C. [$H_2SO_4$] | |
| --- | --- | --- | --- | --- |
| % (v/v) | 6.0 mM | 7.0 mM | 6.0 mM | 7.0 mM |
| 30% | 98.8% | 98.4% | 99.7% | 99.7% |
| 40% | 97.6% | 97.4% | 99.8% | 99.6% |
| 50% | 97.0% | 96.2% | 99.6% | 99.8% |

No samples froze at either condition, remaining liquid throughout the storage period. No indication of physical instability (e.g. gelling, precipitation) was observed in the sample formulations. UHPLC analysis indicated that the samples remained chemically stable across the evaluated moisture range. For samples stored at refrigerated conditions (2-8° C.), there was an observed decline in chemical stability with both increasing moisture content and acid, but overall glucagon purity remained well above 95% following over one year of storage.

Together with those of the preceding Examples, these results indicate that high-moisture DMSO/glucagon formulations can be prepared that exhibit excellent long-term storage stability under both refrigerated and sub-freezing conditions.

All of the compositions and/or methods disclosed and claimed herein can be made and executed without undue experimentation in light of the present disclosure. While the compositions and methods of this disclosure have been described in terms of some embodiments, it will be apparent to those of skill in the art that variations may be applied to the compositions and methods and in the steps or in the sequence of steps of the method described herein without departing from the concept, spirit, and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of any invention as defined by the appended claims.

What is claimed is:

1. A stable aprotic polar solvent formulation comprising:
   (a) a glucagon peptide, glucagon analog, glucagon mimetic, or salt thereof;
   (b) an ionization stabilizing excipient;
   (c) an aprotic polar solvent; and
   (d) a moisture content from about 25% v/v to about 50% v/v, wherein the formulation is compatible with a container and/or injection device flow path.

2. The formulation of claim 1, wherein components of the device flow path comprise rubber, thermoplastic, thermoset plastic, polystyrenes, polyvinyl alcohols, polyvinyl pyrrolidones, polyalkylene oxides, acrylamides, acrylic acids, cellulose, cellulose ethers, cellulose esters, cellulose amides, polyvinyl acetates, polycarboxylic acids, polyamides, polyacrylamide, copolymers of maleic/acrylic acids, polysaccharides, or natural gums, or a combination of two or more thereof.

3. The formulation of claim 2, wherein the components of the device flow path comprise polycarbonate (PC), acrylonitrile butadiene styrene (ABS), meta-acrylonitrile butadiene styrene (MABS), methylcellulose, carboxymethylcellulose sodium, dextrin, ethylcellulose, hydroxyethyl cellulose, hydroxypropyl methylcellulose, maltodextrin, polymethacrylates, polystyrene (PS), polyisobutylene (PIB), polymethyl methacrylate (PMMA), ethylene vinyl acetate (EVA), polyvinyl chloride (PVC), thermoplastic polyurethane (TPU), hydroxypropyl methyl cellulose (HPMC), high density polyethylene (HDPE), low density polyethylene (LDPE), polyurethane, or blends thereof.

4. The formulation of claim 1, wherein the glucagon peptide, glucagon analog, glucagon mimetic, or salt thereof is dissolved in an amount from about 0.1 mg/mL up to the solubility limit of the glucagon peptide, glucagon analog, glucagon mimetic, or salt thereof.

5. The formulation of claim 1, wherein the ionization stabilizing excipient is included in the formulation in an amount to maintain physical stability of the glucagon peptide, glucagon analog, glucagon mimetic, or salt thereof.

6. The formulation of claim 1, wherein the ionization stabilizing excipient is at a concentration of 0.01 mM to less than 200 mM.

7. The formulation of claim 1, wherein the ionization stabilizing excipient is a mineral acid.

8. The formulation of claim 7, wherein the mineral acid is selected from the group consisting of hydrochloric acid, sulfuric acid, and nitric acid.

9. The formulation of claim 1, wherein the aprotic polar solvent is DMSO.

10. The formulation of claim 1, wherein the ionization stabilizing excipient is hydrochloric acid and the aprotic polar solvent is DMSO.

11. The formulation of claim 1, wherein the moisture content is from about 30% v/v to about 40% v/v.

12. The formulation of claim 1, further comprising a preservative at less than about 10% w/v.

13. The formulation of claim 12, wherein the preservative is metacresol.

14. The formulation of claim 1, further comprising a disaccharide at less than about 10% w/v, less than about 5% w/v, or less than about 3% w/v.

15. The formulation of claim 14, wherein the disaccharide is trehalose.

16. The formulation of claim 1, wherein the formulation has a freezing point of less than about 0° C.

17. The formulation of claim 16, wherein the formulation has a freezing point of less than about −20° C.

18. The formulation of claim 16, wherein the formulation has a freezing point of between about −50° C. and about −80° C.

19. The formulation of claim 1, wherein the container or injection device flow path is an infusion set or pump capable of parenterally administering the formulation to a subject.

20. A method of treating hypoglycemia by introducing an effective amount of the formulation of claim 1 into a subject in need thereof.

21. The method of claim 20, wherein the formulation is introduced into said subject via infusion.

22. The method of claim 21, wherein the infusion is accomplished by pump infusion.

23. The method of claim 22, wherein said pump infusion comprises continuous or bolus pump infusion, or a combination thereof.

24. A method of producing a stable glucagon formulation, said method comprising mixing at least one ionization stabilizing excipient, at least one aprotic polar solvent, glucagon, and sufficient water to result in a moisture content in said formulation of between about 25% v/v and about 50% v/v, thereby forming a stable glucagon formulation that is compatible with devices and/or fluid flow paths.

25. The method of claim 24, wherein said moisture content is from about 30% v/v to about 50% v/v.

26. The method of claim 24, wherein said moisture content is about 35% v/v, about 40% v/v, about 45% v/v, or about 50% v/v.

27. The method of claim 24, wherein the ionization stabilizing excipient is at least one mineral acid.

28. The method of claim 27, wherein said mineral acid is hydrochloric acid, nitric acid, sulfuric acid, or a combination thereof.

29. The method of claim 24, wherein the ionization stabilizing excipient concentration is between about 0.1 mM to about 200 mM.

30. The method of claim 29, wherein the ionization stabilizing excipient concentration is between about 1 mM to about 20 mM.

31. The method of claim 29, wherein the ionization stabilizing excipient concentration is between about 1 mM to about 10 mM.

32. The method of claim 29, wherein the ionization stabilizing excipient concentration is between about 4 mM to about 9 mM.

33. The method of claim 24, wherein the aprotic polar solvent is DMSO.

* * * * *